United States Patent
Charan et al.

(10) Patent No.: US 10,762,183 B1
(45) Date of Patent: Sep. 1, 2020

(54) SECURE AUTHENTICATION USING BIOMETRIC FACTORS

(71) Applicant: Architecture Technology Corporation, Minneapolis, MN (US)

(72) Inventors: Deborah K. Charan, Minneapolis, MN (US); Ranga Ramanujan, Medina, MN (US)

(73) Assignee: ARCHITECTURE TECHNOLOGY CORPORATION, Minneapolis, MN (US)

( * ) Notice: Subject to any disclaimer, the term of this patent is extended or adjusted under 35 U.S.C. 154(b) by 184 days.

(21) Appl. No.: 15/866,046

(22) Filed: Jan. 9, 2018

Related U.S. Application Data

(60) Provisional application No. 62/489,325, filed on Apr. 24, 2017.

(51) Int. Cl.
*G06F 21/32* (2013.01)
*A61B 5/0402* (2006.01)
*G06K 9/00* (2006.01)

(52) U.S. Cl.
CPC ............ *G06F 21/32* (2013.01); *A61B 5/0402* (2013.01); *G06K 9/00221* (2013.01); *G06K 9/00557* (2013.01)

(58) Field of Classification Search
CPC ............... G06F 19/328; G06F 19/3418; G06F 21/6245; G06F 21/6227; G06F 21/35; G06Q 10/10; G06Q 50/24; G06Q 20/367; G06Q 20/3674; G06Q 20/382; G06Q 30/0283; G16H 10/60; G16H 10/65; H04L 63/0861; H04L 63/1425; H04L 2209/56; H04L 2209/608; H04L 2209/805; H04L 2209/88; H04L 63/0442; H04L 63/061; H04L 9/0825; H04L 9/0841; H04L 9/302; H04L 9/321; H04L 9/3249;
(Continued)

(56) References Cited

U.S. PATENT DOCUMENTS 8,561,142 B1   10/2013   Sobel
8,970,348 B1   3/2015    Evans et al.
(Continued)

OTHER PUBLICATIONS

"Gartner Says Worldwide Information Security Spending will Grow 7 Percent to Reach $86.4 Billion in 2017," gartner.com, Aug. 16, 2017, 4 pp.
(Continued)

*Primary Examiner* — Abiy Getachew
(74) *Attorney, Agent, or Firm* — Shumaker & Sieffert, P.A.

(57) ABSTRACT

In general, the techniques of this disclosure describe a computing device in a secure domain that is configured to receive, via a guard device, an authentication factor from a biometric authentication device in a non-secure domain. The biometric authentication device is in a non-secure domain, and the authentication factor comprises an identifier of a prospective user of the biometric authentication device. The computing device may then determine, based on the received authentication factor, whether the prospective user is a trusted user of the computing device based on the authentication factor. Responsive to determining that the prospective user of the biometric authentication device is the trusted user, the computing device may enable access to one or more applications on the computing device.

15 Claims, 10 Drawing Sheets

(58) Field of Classification Search
CPC ........... H04W 12/00522; H04W 12/06; H04W 12/12; G06K 9/00369; H04N 21/4318; H04N 21/44008; H04N 21/44222; H04N 21/4668; H04N 21/475; H04N 7/163; G07C 2009/00365; G07C 2009/00388; G07C 2009/00412; G07C 9/00309; G07C 9/00563; G07C 9/28
See application file for complete search history.

(56) References Cited

U.S. PATENT DOCUMENTS

| | | | |
|---|---|---|---|
| 9,419,799 | B1 | 8/2016 | Chung |
| 10,091,230 | B1 | 10/2018 | Machani et al. |
| 10,164,974 | B2 | 12/2018 | Spencer et al. |
| 2014/0157381 | A1 | 6/2014 | Disraeli |
| 2014/0304773 | A1 | 10/2014 | Woods et al. |
| 2015/0161370 | A1 | 6/2015 | North et al. |
| 2015/0281225 | A1 | 10/2015 | Schoen et al. |
| 2015/0363582 | A1* | 12/2015 | Sheller ................ G06F 21/31 726/17 |
| 2016/0233946 | A1 | 8/2016 | Wengrovitz et al. |
| 2016/0241523 | A1* | 8/2016 | Ahn .................... H04L 9/0894 |
| 2017/0193211 | A1 | 7/2017 | Blake et al. |
| 2017/0242995 | A1 | 8/2017 | Bassenye-Mukasa et al. |
| 2018/0054312 | A1* | 2/2018 | Kamal ................ H04L 9/3231 |
| 2018/0095900 | A1* | 4/2018 | Sarangdhar ......... G06F 12/1425 |

OTHER PUBLICATIONS

"Harris Still in Neutral Zone," Zacks Equity Research, Feb. 13, 2012, 2 pp.
"Military Communications Market Worth USD 40.82 Billion by 2020," MarketWatch, Sep. 11, 2015, 2 pp.
"Military Tablet Wars: Windows Gaining on Apple," Kiosk Industry, Feb. 27, 2016, 1 pp.
De Renesse, "Virtual Digital Assistants to Overtake World Population by 2021," informa.com, May 17, 2017, 3 pp.
Office Action from U.S. Appl. No. 15/870,492, dated Sep. 5, 2019, 13 pp.
"Multi-Factor Authentication," Wikipedia, the free encyclopedia, retrieved from https://en.wikipedia.org/wiki/Multi-factor_authentication, Jan. 18, 2018, 8 pp.
Joint Tactical Radio System, Wikipedia, the free encyclopedia, retrieved from https://en.wikipedia.org/wiki/Joint_Tactical_Radio_System, Jan. 18, 2018, 9 pp.
"Equipping the Warfighter with Small Business Ingenuity," Phase III Desk Reference,V1.0, U.S. Air Force, 2016 (Applicant points out, in accordance with MPEP 609.04(a), that the year of publication, 2016, is sufficiently earlier than the effective U.S. filing date 2018, so that the particular month of publication is not in issue.) p. 16.
"Technavio Says Global EEG and ECG Biometrics Market Will Reach $42.14 Million by 2020," Technavio.com, Apr. 7, 2016, 2 pp.
Keller, "ATCorp to build SWaP-Optimized Airborne Networking Router Prototypes for Carrier-Based Aircraft," Military and Aerospace Electronics, Jan. 19, 2017, 4 pp.
Lugovaya, "Biometric Human Identification Based on ECG," physionet.org, 2005 (Applicant points out, in accordance with MPEP 609.04(a), that the year of publication, 2005, is sufficiently earlier than the effective U.S. filing date, 2018, so that the particular month of publication is not in issue.) 9 pp.
"A Heart to my Key," economist.com., https://www.economist.com/blogs/babbage/2013/05/biometrics, May 9, 2013, 4 pp.
"NYMI Band: Product Overview," Nymi, retrieved from https://nymi.com/product_overview, on Jan. 18, 2018, 2 pp.
U.S. Appl. No. 15/870,492, filed Jan. 12, 2018, by Burnett et al.
U.S. Appl. No. 15/866,097, filed Jan. 9, 2018, by Bonney et al.
U.S. Appl. No. 62/489,320, by Ranga Ramanujan et al., filed May 3, 2017.
U.S. Appl. No. 15/959,709, filed Apr. 23, 2018, by Ramanujan et al.
Final Office Action from U.S. Appl. No. 15/870,492, dated Feb. 12, 2020, 15 pp.
Office Action from U.S. Appl. No. 15/866,097, dated Mar. 4, 2020, 20 pp.
Advisory Action from U.S. Appl. No. 15/870,492, dated Apr. 17, 2020, 3 pp.
Response to Final Office Action dated Feb. 12, 2020, from U.S. Appl. No. 15/870,492, filed Apr. 7, 2020, 14 pp.
Response to Office Action dated Sep. 5, 2019, from U.S. Appl. No. 15/870,492, filed Nov. 25, 2019, 15 pp.
Response to Office Action dated Mar. 4, 2020, from U.S. Appl. No. 15/866,097, filed Jun. 4, 2020, 15 pp.

\* cited by examiner

SECURE AUTHENTICATION USING BIOMETRIC FACTORS

This application claims the benefit of U.S. Provisional Application No. 62/489,325, filed Apr. 24, 2017, the entire content of which is incorporated herein by reference.

STATEMENT REGARDING FEDERALLY SPONSORED RESEARCH OR DEVELOPMENT

This invention was made with Government support under Contract W81XWH-18-C-0012 awarded by the United States Army Medical Research Acquisition Activity. The Government may have certain rights in this invention.

TECHNICAL FIELD

The disclosure relates to handling and processing secured data.

BACKGROUND

Field-users of secure mobile devices may employ multiple digital assets in the field for digital communications and other applications. Examples may include voice applications and surveillance unmanned aerial vehicles (UAVs). Some data sources do not support any secured level classification. Some integrated systems may utilize commercial off-the-shelf (COTS) devices for secured level tactical and front-line use (e.g., common operating picture, data feeds, real-time communications, etc.). Even though the non-secured data sources may improve the effectiveness of field-users and improve the ability to complete missions, these systems may not be capable of connecting with secured devices because of the difference in security classification levels. For instance, rules governing the operation of secure devices may preclude direct connection of such devices to non-secure devices or devices at a different classification level than the secured device. As such, the system may block the non-secured data from flowing into the secured domain and may control or block any/all data flowing into the non-secured domain.

SUMMARY

In general, the techniques of this disclosure describe a computing device that is configured to verify an identity of a user based on an authentication factor (e.g., a biometric authentication factor) received from an authentication device. The computing device may receive an authentication factor from an authentication device via a guard device. A guard device may be any standalone device, hardware component, or software component that receives information from a device that is in a non-secure domain (e.g., as part of a system of devices that have not been tested and/or verified as being secure and are unable to communicate directly with the computing device), and forwards the information to a computing device in a secure domain. In some instances, the guard device may further analyze the information to ensure its integrity (e.g., part of a system of one or more devices that have been deemed secure and that may communicate with other devices within the domain without requiring the data packets to be scrutinized). The computing device may determine whether the prospective user is a trusted user of the computing device based on the authentication factor. If the computing device determines that the prospective user of the authentication device is the trusted user, the computing device may enable access to one or more applications on the computing device.

In one example, the disclosure is directed to a method including receiving, by a computing device in a secure domain via a guard device, an authentication factor from a biometric authentication device. The biometric authentication device is in a non-secure domain, and the authentication factor comprises an identifier of a prospective user of the biometric authentication device. The method further includes determining, by the computing device, whether the prospective user is a trusted user of the computing device based on the authentication factor. The method further includes, responsive to determining that the prospective user of the biometric authentication device is the trusted user, enabling, by the computing device, access to one or more applications on the computing device.

In another example, the disclosure is directed to a computing device comprising one or more communication units configured to receive, via a guard device, an authentication factor from a biometric authentication device. The computing device is located in a secure domain. The biometric authentication device is in a non-secure domain, and the authentication factor comprises an identifier of a prospective user of the biometric authentication device. The computing device further includes one or more processors. The one or more processors are configured to determine whether the prospective user is a trusted user of the computing device based on the authentication factor. The one or more processors are further configured to, responsive to determining that the prospective user of the biometric authentication device is the trusted user, enable access to one or more applications on the computing device.

In another example, the disclosure is directed to a non-transitory computer readable storage medium storing instructions that, when executed by one or more processors of a computing device cause the one or more processors to receive, via a guard device, an authentication factor from a biometric authentication device. The computing device is located in a secure domain. The biometric authentication device is in a non-secure domain, and the authentication factor comprises an identifier of a prospective user of the biometric authentication device. The instructions further cause the one or more processors to determine whether the prospective user is a trusted user of the computing device based on the authentication factor. The instructions further cause the one or more processors to, responsive to determining that the prospective user of the biometric authentication device is the trusted user, enable access to one or more applications on the computing device.

In another example, the disclosure is directed to a system including means for receiving, in a secure domain, via a guard device, an authentication factor from a biometric authentication device. The biometric authentication device is in a non-secure domain, and the authentication factor comprises an identifier of a prospective user of the biometric authentication device. The system further includes means for determining whether the prospective user is a trusted user of the computing device based on the authentication factor. The system further includes, responsive to determining that the prospective user of the biometric authentication device is the trusted user, means for enabling access to one or more applications on the computing device.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
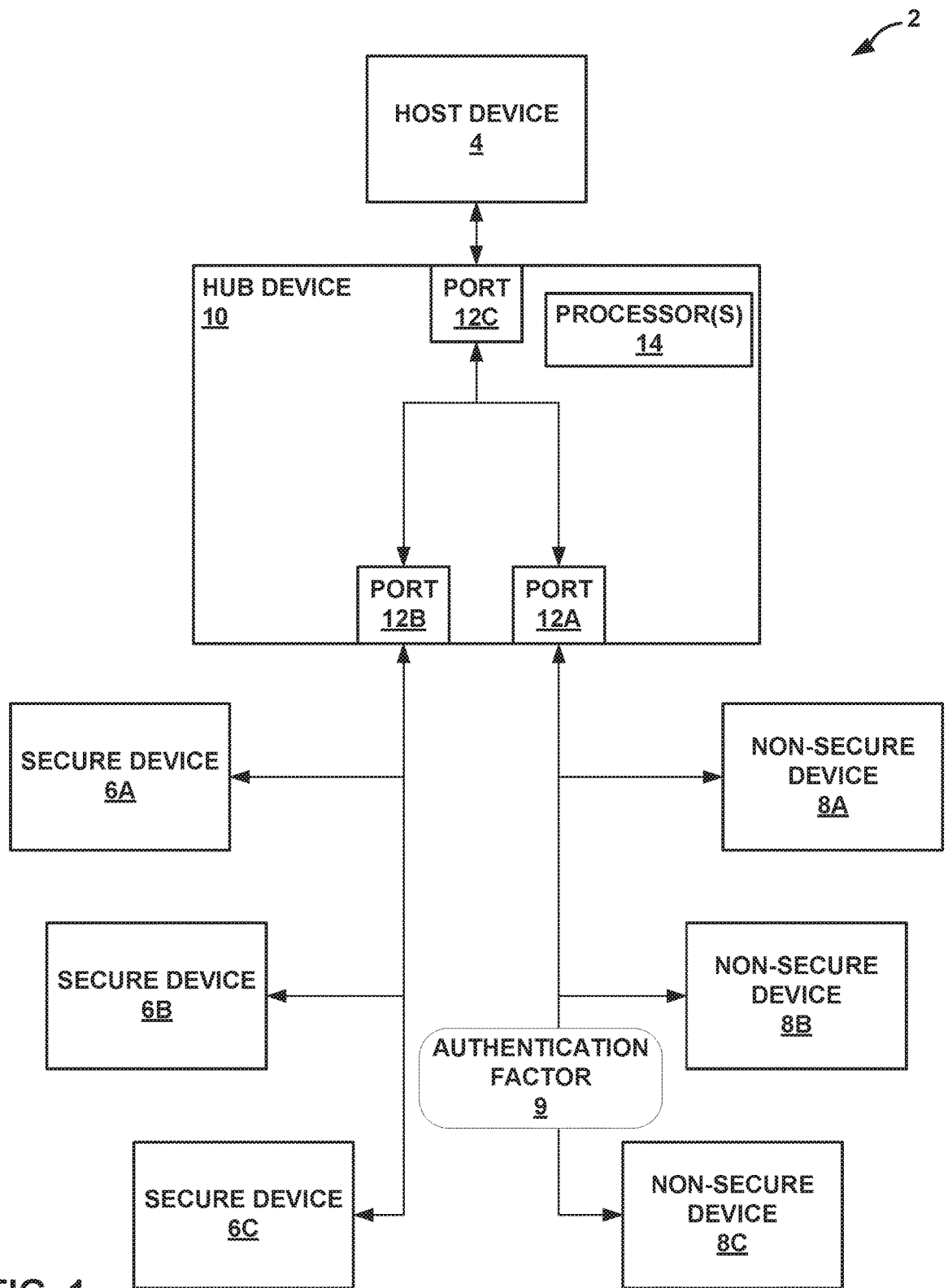
FIG. 1 is a block diagram illustrating an example of a hub device configured to receive data packets from both secure client devices and non-secure client devices and to forward the received data packets to a host device, in accordance with one or more techniques of this disclosure.

In general, this disclosure describes techniques for authenticating an identity of a user using a system that includes a biometric authentication device, a guard device (e.g., implemented in a hub device), and a client device (e.g., a host device or other end user device). The biometric authentication device, which is in a non-secure domain and attached to a prospective user of the client device (e.g., an extremity of the user, a head of the user, or a torso of the user), may create an authentication factor (e.g., a signature or biometric information), either through user input or user analysis, for a user that is attempting to access the client device. An embedded processor in the guard device or a software-based data diode operable by the guard device may receive the authentication factors and, after potentially ensuring the security of the data, forward the authentication factors to the client device, which is in a secure domain. The client device may then determine whether the prospective user is a trusted user of the computing device based on the authentication factor. Responsive to determining that the prospective user of the biometric authentication device is the trusted user, the computing device will enable access to one or more applications on the computing device. Conversely, responsive to determining that the authentication factor does not correspond to the particular trusted user, that the determined user does not have a particular level of security clearance, or determining that the user is not recognized, the computing device may disable access to the one or more applications on the computing device. In some examples, after the prospective user has access to the client device, the client device may receive additional authentication factors from other users to determine an identity of the other user(s).

In cases where a user in the field (i.e., apart from a control/technological center that houses devices with higher processing power and effectively unlimited resources) is attempting to access a client device that operates in a secure domain, such as tactical networks with classified environments, authentication of the user may be required before access to the client device is granted. Even upon grant of access, the identity and security classification of the user may limit access to particular features or applications of the client device, as opposed to unhindered use of the client device. Further, requiring complex password entry in such situations could be overly cumbersome to a user who needs immediate access to the locked device. Authentication devices may be added to the system to provide this needed authentication. However, if the authentication devices are also to be in the secure domain, each authentication device would have to undergo expensive and time-consuming modification to operate in such a manner. If the authentication devices are to be cheaper, off-the-shelf devices that operate in a non-secure domain, allowing communication between the authentication devices and the client device directly may lead to security issues and greater instances of hacking attempts.

Furthermore, if the user is credentialed as a medic, the user may need to provide medical assistance to other users in the field. However, discerning the identity of other users in the field may be difficult, as the other users may be unresponsive, carrying inaccurate or unreliable identification, unfamiliar to the medic, or in a state where visual identification is ineffective. Further, if the other user is carrying electronic identification, the electronic identification may have the same problems as the authentication devices listed above with regards to security and authenticity.

As such, the techniques of this disclosure describe utilizing an embedded processor in the guard (or "hub") device or a software-based data diode operable by the guard device that may be in communication, either through a wireless interface or a wired interface, with a plurality of different authentication devices. A biometric authentication device may send the authentication factor to the guard device, which analyzes the authentication factors for safety and integrity before forwarding the authentication factors to the client device. For the purposes of this disclosure, the terms "client device," "host device," and "end user device" may be used interchangeably to mean any computing device, in a secure domain, that may perform the authentication verification process described herein.

By sending the authentication factors through the guard device, the client device may ensure safety of the data it is receiving from the authentication devices, which are in a non-secure domain. Further, the client device may be particularly configured to store authentication factors for multiple users and perform authentication on numerous authentication devices, enabling the client device to perform with minimal additional devices for the specific authentication required in tactical networks. The client device may also store medical information, where, after the user is confirmed and the client device enables access for the user, the client device may receive subsequent authentication factors from biometric authentication devices for another user, verify the other user's identity, and retrieve medical information for treating the other user based on their identity.

This disclosure further describes a hub device that is configured to receive data packets from both secured client devices and non-secured client devices. In situations where authentication devices, that may not be in a secure domain, send authentication factors to client devices in a secure domain, a hub device, such as the hub device described herein, may be used to enable communication of said non-secure authentication factors to the secure client device in a secure manner. In some instances, the hub device may send the data packets from the secured client devices straight to a secured host device, as secured client devices may be implicitly trusted within the overall system of devices in the information exchange. In other instances, the hub device may perform some preliminary processing of the secure data packets, such as determining a sender of the data packets or the type of contents within the data packets. For the data packets originating from the non-secured authentication or computing devices, the hub device may first process the data packets to ensure the integrity of the received non-secure data packets. Generally, the hub device may process and route non-secure traffic according to some pre-defined guard process based on the particular non-secure source. For instance, the hub device may perform a virus scan and/or some other integrity check on the non-secure data packets prior to sending the non-secure data packets to the host device such that the hub device blocks unsafe data packets or infiltration attempts from outside devices being forwarded to the host device.

Other devices may simply block all non-secured data from reaching the host device entirely. However, the non-secured data may still include critical information necessary for the host device. As such, blocking the data entirely may be detrimental. Other devices, however, may analyze the non-secured data once it reaches the host device. However, due to the potential damaging nature of non-secured data, malicious or virus-laden data may damage the host device to the point of where the host device may be useless or compromised.

Rather than blocking non-secured data either entirely or not at all, the techniques described herein may provide heightened one-way filtering of incoming data packets/streams received from non-secured client devices (e.g., transmission control protocol (TCP) data flows and user datagram protocol (UDP) data flows). Further, a single hub device may interconnect multiple data sources, both secured and non-secured, across multiple ports to the secured host device. A single hub device also implies a single configuration interface. The hub device, for example, may be a computing device with a full central processing unit (CPU), one or more universal serial bus (USB) ports (e.g., 4), one or more Ethernet ports (e.g., 2), and an operating system or a micro-operating system (e.g., the evaluation assurance level (EAL) 7 secure level 4 (seL4) micro-kernel), although other examples of the hub device may include more or fewer ports, different protocols for the ports (e.g., Wi-Fi, Bluetooth, etc.), or a different CPU and/or operating system. The hub device of this disclosure may perform the techniques described herein regardless of the device type, vendor, or operating system used by the end-user host device.

FIG. 1 is a block diagram illustrating an example system 2 that includes hub device 10 configured to receive data packets from both secure client devices 6A-6C and non-secure client devices 8A, 8B, and 8C and to forward the received data packets to a host device 4, in accordance with one or more techniques of this disclosure. In the techniques of the current disclosure, the computing device that performs the authentication techniques described herein may receive the authentication factors, such as authentication factor 9, from biometric authentication devices, such as non-secure client device 8C, via a hub device, such as hub device 10. System 2 is shown to include host device 4, secure client devices 6A-6C (collectively, secure client devices 6), non-secure client devices 8A, 8B, and 8C (collectively, non-secure client devices 8), and hub 10. This specific arrangement of devices, however, is only a single example configuration of system 2. In other configurations, there may be more secure/non-secure client devices or less (as few as zero) secure/non-secure client devices operably connected to hub 10 than shown in FIG. 1.

Host device 4 is an end-user device (EUD) in a secure domain described below, for purposes of illustration only, as a tablet computer. However, in some examples, host device 4 may be a computerized watch (e.g., a smart watch), computerized eyewear, computerized headwear, other types of wearable computing devices, a smartphone, a personal digital assistant (PDA), a laptop computer, a media player, a television platform, an automobile navigation system, a digital camera, or any other type of mobile and/or non-mobile computing device that is configured to perform a media operation as described herein.

Secure client devices 6 may be any device configured to send data packets to hub 10 over a secured channel (e.g., a hard-wired connection or a closed/protected network connection) and further configured to operate in accordance with a trusted secure security classification, such as secret, top secret, classified, or protected. Examples of secure client devices 6 may include a secured radio device, a secured global positioning system receiver device, any computing device configured to operate in accordance with an encryption protocol also used by host device 4, a computing device configured to utilize steganography to write a particular string of data within a data packet, any computing device that has been approved for secure status (e.g., an approved surveillance drone, an approved UAV, an approved video feed, an approved biometric sensor, etc.), or any other computing device configured to operate with some threshold level of security such that host device 4 may implicitly trust the data packets received from secure client devices 6.

Non-secure client devices 8 may be any device configured to send data packets to hub 10 over a non-secured channel (e.g., an open network or an unprotected network) or a channel with unknown security. Further, non-secure client device 8 may not be configured to operate in accordance with a trusted secure security classification or it may be unknown to hub 10 and host device 4 as to whether non-secure client devices 8 are configured to operate in accordance with a trusted secure security classification. Examples of non-secure client devices 8 may include a UAV, a general data producing device not configured to operate in accordance with a trusted security protocol, video and voice applications, anonymous cellular phones, landline telephones, anonymous Internet devices, any computing device that has not been approved for secure status (e.g., a non-approved surveillance drone, a non-approved video feed, a non-approved biometric sensor, etc.), biometric sensors, or any other untrusted or potentially unsafe computing device.

For the purposes of this disclosure, hub 10 may be any device capable of receiving data from and sending data to computing devices in different security domains (i.e., host device 4 and secure client devices 6 or non-secure client devices 8). Hub 10 may be configured to utilize one or more different communication protocols for receiving and sending the data packets, including Wi-Fi (e.g., the Institute of Electrical and Electronics Engineers (IEEE) 802.11 standard), the Bluetooth protocol, various radio frequency communication devices and waveforms, USB, the Ethernet industrial protocol, radio waves/frequencies, the Internet protocol suite, Java remote method invocation, dynamic data exchange, or any other communication protocol suitable for exchanging secure and non-secure data packets.

Hub 10 may include three or more ports 12A. 12B, and 12C (collectively, ports 12). Ports 12 may serve as an interface between hub 10 and other computers or peripheral devices (e.g., host 4, secure client devices 6, and non-secure client devices 8). In some examples, ports 12 may refer to a physical connection, and in other examples, ports 12 may refer to logical or wireless connections. Electronically, when ports 12 refer to a physical connection, several conductors where ports 12 and a physical cable contacts connect may provide a method to transfer signals between devices. In other examples, ports 12 may refer to a portion of hub 10 configured to wirelessly connect with other computing devices in order to exchange information and data packets/streams.

Hub 10 may further include one or more processors 14. One or more processors 8, in one example, are configured to implement functionality and/or process instructions for execution within hub 10. For example, processors 14 may be capable of processing instructions stored in a storage device of hub 10. Examples of processors 14 may include, any one or more of a microprocessor, a controller, a digital signal processor (DSP), an application specific integrated circuit (ASIC), a field-programmable gate array (FPGA), or equivalent discrete or integrated logic circuitry.

In accordance with the techniques of this disclosure, processors 14 of hub 10 may receive, via port 12A, a first data packet from non-secure client device 8A. For instance, non-secure client device 8A may be a data producing device not configured to operate in accordance with a trusted or secure protocol. For instance, a secure protocol may include the IPsec protocol or another encapsulating security payload (ESP) protocol, among other things. Conversely, the non-secure data producing protocols may include the real-time protocol (RTP) for voice or audio, the voice over internet protocol (VoIP), or the file transfer protocol (FTP), among other things. However, non-secure client device 8A may generate information that would be beneficial to transmit to host 4. As such, non-secure client device 8A may transmit the data packets to hub 10 via port 12A.

Processors 14 of hub 10 may also receive, via port 12B, a second data packet from secure client device 6A. For instance, secure client device 6A may be a radio that transmits data packets wirelessly to hub 10 over a channel that uses a trusted or secure protocol. Host 4 may request a status update from a user of secure client device 6A, and secure client device 6A may respond by transmitting the data packets to hub 10 via port 12B.

In some examples, based on the sender of the respective data packet, processor 14 may perform separate guard processes on the respective data packets. For instance, processors 14 may perform a first guard process on the first data packet based on the security classification of non-secure client device 8A (i.e., non-secure or untrusted) and perform a second guard process on the second data packet based on the security classification of secure client device 6A (e.g., a secure security classification, such as secret, top secret, classified, or protected). For the second guard process, in some instances, processors 14 may simply forward the second data packet to host 4 via port 12C. In other instances, for the second guard process, processors 14 may analyze contents of the second data packet to determine an identity of the sender of the second data packet or the type of contents in the second data packet prior to forwarding the second data packet to host 4 via port 12C. As the second data packet may come from a secure and trusted client device, processors 14 may refrain from determining an integrity of the received data and performing a virus scan operation on the second data packet. As described in greater detail below with respect to FIG. 2, the first guard process may include performing an integrity check and/or a virus scan, or, generally, a heightened filtering process.

Processors 14 of hub 10 may send, via port 12C, the first data packet from non-secure client device 8A and the second data packet from secure client device 6A to host 4. Port 12C may forward the respective data packets to host 4 either upon receipt of the respective data packets or after the respective data packets have been processed. In other words, port 12C may not necessarily forward the first data packet and the second data packet simultaneously, but instead forward the first data packet and the second data packet after processors 14 determines the respective data packet to be safe to forward to host 4 in the respective data packet's own respective processing loop. The timing with which processors 14 forward the first data packet is independent of the timing with which processors 14 forward the second data packet.

In some examples, processors 14 may simply forward the first data packet and the second data packet to host 4 upon receiving the respective data packets. In other examples, as described above, processors 14 may implement some form of guard process to evaluate the first data packet received from non-secure client device 8A. Upon determining that the first data packet meets a threshold level of integrity, processors 14 may forward the first data packet to host 4 via port 12C. In still other instances, processors 14 may process certain information regarding the second data packet (i.e., sender information or content information) prior to forwarding the second data packet to host 4.

In some examples, in addition to the one-way guard functionality described throughout this disclosure, hub 10 may also analyze data packets intended to be sent to non-secure client devices 8 or secure client devices 6, providing two-way guard functionality. For instance, processors 14 of hub 10 may receive an outgoing message to be sent to non-secure client devices 8 or secure client devices 6. For instance, if the outgoing message is intended for one of secure client devices 6, processors 14 of hub 10 may forward the outgoing message to the one of secure client devices 6 without restriction or with restrictions based on the respective trust level of the one of secure client devices 6. In other instances, host 4 may attempt to send an ACK message, or an acknowledgement message that verifies the receipt of the incoming data packets, to non-secure client device 8A. However, in response to determining that the outgoing message contains secure information, processors 14 of hub 10 may refrain from sending the outgoing message to non-secure client device 8A so as to protect the integrity of the secured system. In other instances, however, processors 14 of hub 10 may scan the outgoing message to determine whether the outgoing message contains secure information that would be improper for a non-secure client device to receive. In response to determining that the outgoing message does not contain secure information, processors 14 of hub 10 may send the outgoing message to non-secure client device 8A via port 12A. Processors 14 may only send the outgoing messages to the non-secure client devices 8A and/or 8B when a security policy has been set up with approvals to send such messages to the respective non-secure client devices.

In some other examples, rather than expecting host 4 to produce and send ACK messages, processors 14 may utilize a proxy module to produce an ACK message. If processors 14 still receive the ACK message from host 4, processors 14 may block the received ACK message and utilize a proxy module to produce an ACK instead. For instance, if the first data packet was part of a TCP conversation, processors 14 may utilize the proxy module to create an ACK message and send the ACK message to non-secure client device 8A. In creating a separate ACK message at processors 14, hub 10 may maintain a one-way communication between host 4 and the non-secure client device, as the non-secure client device will not receive any data created by host 4.

In other examples, processors 14 of hub 10 may prevent all outgoing traffic from reaching non-secure client device 8A. In such examples, processors 14 of hub 10 may receive an outgoing message to be sent to non-secure client device 8A. Upon determining that the intended recipient of the outgoing message is a non-secure client device (i.e., non-secure client device 8A), processors 14 of hub 10 may refrain from sending the outgoing message to non-secure client device 8A so as to protect the operation and safety of the secured system.

Hub 10 is one example of a device that may perform one-way guard functions to enable communication between devices in a non-secure domain (e.g., non-secure client devices 8) and a device in a secure domain (e.g., host 4). Although the techniques of this disclosure are described with respect to hub 10, any computing device that may perform similar one-way guard functions to process data packets received from a non-secure device and forward the non-secure data packets to a secure host device may be similarly utilized to perform the techniques of this disclosure. While authentication between devices is solved simply in the consumer world, the tactical world provides a more difficult authentication environment. For instance, wireless interfaces (e.g., wireless internet or radio frequencies) are disabled on host devices as part of military security regulations in an effort to reduce the cyber-attack surface of host 4 and to prevent unintended leakage of sensitive data from the secure host. Further, authentication devices may be non-secure devices (e.g., any of non-secure client devices 8), meaning that direct communication between the authentication devices and host 4 may be blocked or restricted. Hub 10, or any other device that may perform one-way guard functions, may enable the authentication devices to send authentication factors to host 4.

In some examples, host 4 may utilize authentication data, such as biometric information, received from hub 10 with the first data packet as verification for an identity of the user of host 4. For example, a user of host 4 may be a trusted user (e.g., a user within the same organization or a known user having a particular level of security clearance) that is seeking to provide authentication to host 4 in order to gain access to one or more applications on host 4. In some instances, if host 4 is authenticating the user in a hostile situation or a situation where the user must access host 4 very quickly, host 4 may be unable to perform certain authentication processes due to the unavailability of certain authentication factors (e.g., the user is wearing gloves and unable to provide touch input on host 4, or voice authentication is unavailable due to extraneous environmental noise) or the length of time it takes to produce the authentication factor. Further, the various authentication devices may be non-secure devices (e.g., any of non-secure client devices 8), complicating the exchange of data between the authentication device and host 4.

Instead, the trusted user may be equipped with biometric sensors (e.g., an electrocardiogram (ECG) monitoring bracelet) to verify the trusted user's identity. A typical ECG has five peaks and troughs, which are known as the PQRST pattern, which measures electrical activity in the heart that manifest as P-waves. QRS-complexes, and T-waves. The P-wave represents atrial depolarization of the user's heart, or the electrical event that occurs in the left and right atria of the user's heart prior to contraction of the atria. The P-wave is typically followed by the QRS-complex, which represents ventricular depolarization, or the electrical event that occurs in the left and right ventricles of the user's heart prior to contraction of the ventricles. Finishing the pattern, the T-wave shows a ventricular repolarization, or the electrical event that occurs as the heart relaxes post-contraction and as the heart prepares to start the PQRST pattern over again. An elevated heartbeat may only alter the frequency of the pattern, but typically does not change the shape of an ECG or the pattern. The PQRST pattern also may remain at least similar as the person ages and as they exercise, notwithstanding the effects of diseases on the heart of the user.

The trusted user may have a known PQRST pattern for their ECG stored in memory on host 4. When the trusted user is attempting to transmit data to host 4 via hub 10 and their non-secure device, the biometric sensors (e.g., the ECG monitoring bracelet) may take an ECG measurement of the trusted user. The biometric sensors may then transmit the ECG to hub 10, either itself or via a Bluetooth connected transmitter device, which then forwards the measurement to host 4 after performing a one-way guard process on the received data packets. If the ECG matches the stored ECG for the trusted user, the host device may have access to information related to that user, much in the same way as different personas are used when logging into shared devices. The ECG bracelets themselves also provide second factor authentication, such as gestures or other measurements able to be taken from a wrist of the user, if desired. This information could all be used by host 4 to verify that the user transmitting the data is actually the trusted user.

The ECG authorization may be constant over a period of time. For instance, the biometric sensors may transmit constant ECG information to hub 10 along with the data packets for the non-trusted client device, which is forwarded to host 4. As long as the ECG information continues to match the stored ECG information, host 4 may approve the integrity of the received data packets. If the ECG information does not match, host 4 may determine that the trusted user may have been compromised and deny the received data packets.

The ECG authorization (with or without the additional gestures) may also be utilized as a password for accessing the host device. The host device may constantly confirm that the band is connected (e.g., by receiving data from the band). If the bracelet is taken off, or the user connection is terminated (e.g., by going out of range), the authentication fails, and the host device would automatically lock. This ensures that the end user is who she/he claims to be, and the user has not changed. As soon as the band is out of range, or loses its connection, the host device may lock.

In some examples, the biometric sensors themselves may perform the verification, sending a data packet that identifies the user of the biometric sensors to hub 10 via a low emission radio beacon. Hub 10 may then forward the data packet to the host device. The host device could be configured to store information regarding multiple users. As such, if a medic were to control the host device and come across a wounded user who is also wearing the biometric sensors, the medic could access information about the wounded user using the biometric sensors as their identification. If each user were to wear some type of transmitting beacon, storing just basic information needed for treatment (i.e. name and serial number, or some form of encrypted ID), the database of information stored would be minimal. The application accessed by the medic may survey for beacons. The application executing on the host device would receive a beacon, identify the user, and synchronize with a local database.

While biometrics may be one example of ways that a user may access host device 4, host device 4 and hub 10 may utilize other devices and/or techniques to enable access to one or more applications stored on host device 4. In some examples, hub 10 may forward authentication factors received from various authentication devices (e.g., any of non-secure client devices 8) to a local server device. The local server device may verify an identity of a user of host 4. The local server device may validate and report the authenticity/identity status of users and their platforms using a web of wearable authentication devices, sensors and software and automatically adjust the level of communications allowed from an endpoint based on this information. Specifically, the local server device may receive two or more different authentication factors from respective authentication devices (e.g., any of non-secure client devices 8) to perform the multi-factor authentication process. Some of the received authentication factors may include multiple factors or signatures (e.g., the local server device may analyze a spoken password both for vocal characteristics and the content of the spoken phrase). In some instances, the local server device may select a subset of the received authentication factors that provide the best chance for user identification and analyze only those authentication factors in the identification process.

The techniques described herein may accommodate authentication of single users as well as a group of ad hoc users, while blocking others (i.e., enable identity based authentication as well as role-based authentication). Traditionally, this is accomplished using an authentication server operated by the enterprise within a remote facility. In a communication challenged tactical environment subjected to disconnected operations, reach-back to a backend server may not always be possible. These techniques overcome this problem using a fully distributed web of wearable authentication micro-servers (e.g., any of secure client devices 6) in the secure domain to provide mission assured authentication.

The local server (e.g., any of secure client devices 6) may use input from multiple sensors within vehicles, mounted outside of vehicles, and carried on users. Some options for these sensors include a voice recognition sensor, a global positioning system receiver, a shoe tap input sensor (e.g., a force sensor attached to a shoe of a user to measure taps), a finger tap input sensor (e.g., a force sensor attached to a hand of a user to measure taps), a hand geometry sensor (e.g., a sensor that may measure the shape of a user's hand), a hand grip sensor (e.g., a sensor to detect various grip characteristics of a user's hand), a fingerprint sensor (e.g., a sensor that may take an image of a user's fingerprint), an electrocardiogram (ECG) sensor (e.g., a sensor that may measure a user's heartbeat and create an ECG based on the measurements), an ear print sensor (e.g., a sensor that may take an image of a user's ear), a radio frequency identification tag, a proximity sensor, a password entry device, a radio device, a gait sensor (e.g., a sensor that measures characteristics of how a user walks) (local and remote), or a keystroke analyzer device. At least three authentication devices may produce one or more of a passcode, signature, profile data, biometric information, or other authentication data that can be stored on a security device. These sensors may connect to a local server device, that may be wearable, or an authentication micro-server through wired and wireless connections creating a web of sensors which feed the device with a variety of authentication factors to be used to perform multi-factor authentication.

This web of sensors provides inputs to the local server device. The local server device collects inputs then compares them against existing known signatures, prints, and profiles contained on the local server device and on nearby cloud servers (within a local mission network) to determine a probability that a person or vehicle are still under control and are who they represent. In some instances, the local server device may also send the inputs to a remote server device for further analysis and confirmation. The local cloud servers contain limited data for a smaller group of users, while remote cloud servers would be able to contain many more profiles and signatures. These profiles and signatures allow for ad hoc users and groups to authenticate dynamically as mission realities change. By including redundancy with low network overhead to counter falsified or hacked signatures, an adversary might be able to compromise a single or small number of units, but not all units, and eventually the local server device redundancy will find discrepancies.

In addition to sensors for positive identification of soldiers and vehicles, sensors may also determine liveness (e.g. heart rate, body temperature, respiratory) as well as detect unknown people. The local server device (or any other device configured to perform the authentication techniques described herein) may adjust the risk probabilities in such a situation. For example, a proximity sensor (and/or occupancy sensor or multiple motion and proximity sensors around a vehicle) could be used to count the number of people nearby, then compare to known radio frequency identifications (RFIDs) of coalition soldiers to count a number of possible unknown people (vs. valid RFIDs or valid/known gait profiles). As the number of unknown people increases, the risk of compromise increases and a higher authentication threshold may be required. In some instances, this number of unknowns can be conveyed to remote users for situational awareness.

In accordance with the techniques of this disclosure, the local server device may receive, in a secure domain and via hub 10, an authentication factor from at least three authentication devices of a group of three or more authentication devices. Each respective authentication device in the group of three or more authentication devices is in a non-secure domain. Further, each respective authentication factor comprises a respective identifier of a respective user of the respective authentication device. The local server device may determine a probability that the respective user of each respective authentication device is a particular trusted user and compare the probability to a threshold authentication probability based on the received authentication factors. Responsive to determining that the probability exceeds the threshold authentication probability, the local server device may enable access to one or more applications on host 4 by sending an authentication confirmation to host 4. In some instances, in addition to performing the authentication locally, the local server may also send the received authentication factors to a remote server for additional confirmation and only enable access to the applications on host 4 once the additional confirmation is received from the remote server.

Conversely, responsive to determining that the probability does not exceed the threshold authentication probability, in some instances, the local server device may disable the access to one or more applications on host 4. In other instances, responsive to determining that the probability does not exceed the threshold authentication probability, the local server may attempt to send the authentication factors and a request to verify the identity of the respective user of the respective authentication device to a remote server and receive one of the identity of the respective user of the respective authentication device or an indication that an untrusted user attempted to gain access to host 4. The local server device may also disable a login credential for the particular user if the probability does not exceed the threshold authentication probability.

These techniques may use multiple identification parameters that, in combination, speed access to host 4 while ensuring reliable, strong authentication. Biometric sensors that may be utilized with these techniques include a voice recognition sensor, a global positioning system receiver, a shoe tap input sensor, a finger tap input sensor, a hand geometry sensor, a hand grip sensor, a fingerprint sensor, an electrocardiogram sensor, an ear print sensor, a radio frequency identification tag, a proximity sensor, a password entry device, a radio device, a gait sensor, or a keystroke analyzer device. At least one authentication device may produce one or more of a passcode, a signature, profile data, authentication data that may be stored on a security device, or biometric information. The authentication factors may also include information that identifies a user as being part of a particular group, and the access granted to the user is in line with general permissions granted to users of that group (e.g., the user is a medic, granting them access to medical information).

The local server device may intermittently request updates from each of the authentication devices in order to continually verify the identity of the user accessing host 4. In such instances, after sending the authentication confirmation to the client device, the local server device may send, to each of the authentication devices, a request for an updated authentication factor. After receiving the updated authentication factors, the local server device may repeat the above authentication process.

In other examples, host device 4 may itself store the data needed to verify the identity of the prospective user. As such, host 4 may quickly authenticate a user based on authentication factors received from a plurality of authentication devices via hub 10. Host device 4 may request input of a strong password (or combination of authentication factors) at power-on. After periods of inactivity that turn off a screen of host 4 to conserve battery and invoke the screen lock, host 4 may require re-authentication before enabling access to one or more applications on host 4. In some instances, host 4 may examine a combination of other authentication factors, other than the strong password and decide to unlock the screen and enable application access internally based on the results of these other authentication factors. Examples of these additional authentication factors include biometric signatures such as heart monitors (e.g., ECG measurements), facial recognition (e.g., photographic analysis of characteristics of the user's facial features), voice recognition (e.g., measuring pitch, volume, pronunciation, and other characteristics of the voice of the user), or stride (e.g., individual "gait" or walk/run pattern) analysis. In general, the authentication factors may be dynamic in the sense that the specific combination of authentication factors required for enabling access to host 4 may be configurable and reconfigurable.

These biometric signatures can be augmented with additional authentication factors, such as digital certificates that are stored on the user's radio frequency identification (RFID) tags. By using multi-factor authentication, host 4 may enable access quickly, easily, and with high confidence that the right user is gaining access to host 4. Further, since the authentication factors are configurable and reconfigurable, host 4 may be configured to utilize optimal mission-specific authentication factors.

As such, hub 10 may include a software-based data diode (or any other device or software that may perform one-way guard functions described herein) and an embedded processor that incorporates its own low-power radio frequency (RF) transceiver that can communicate with biometric sensors. By only letting data travel wirelessly from the biometric sensor (low side) to hub 10 and then to host 4 over a wired connection, and by ensuring that no data can traverse the opposite path, these techniques provide a way to incorporate non-secure biometric sensors for fast user authentication in a secure fashion that is acceptable to cyber-security professionals.

In accordance with the techniques of this disclosure, host 4 may receive, in a secure domain and via hub 10, an authentication factor from two or more (e.g., three) authentication devices of a plurality of authentication devices. Each respective authentication device in the plurality of authentication devices is in a non-secure domain. Further, each respective authentication factor comprises a respective identifier of a respective user of the respective authentication device. Host 4 may determine whether the respective user of each respective authentication device is a particular trusted user based on the received authentication factors. Responsive to determining that the respective user of each respective authentication device is the particular trusted user, host 4 may enable access to one or more applications on host 4. Conversely, responsive to determining that the respective user is not the particular trusted user, host 4 may disable the access to the one or more applications on the computing device.

These techniques may use multiple identification parameters that, in combination, speed access to host 4 while ensuring reliable, strong authentication. Biometric sensors that may be utilized with these techniques include a voice recognition sensor, a global positioning system receiver, a shoe tap input sensor, a finger tap input sensor, a hand geometry sensor, a hand grip sensor, a fingerprint sensor, an electrocardiogram sensor, an ear print sensor, a radio frequency identification tag, a proximity sensor, a password entry device, a radio device, a gait sensor, or a keystroke analyzer device. At least one authentication device may produce one or more of a passcode, data stored on a security device, or biometric information.

Host 4 may determine that the respective user of each respective authentication device is the particular trusted user by comparing each received authentication factor to a respective baseline authentication factor for the particular trusted user and determining that the respective user of each respective authentication device is the particular trusted user if each received authentication factor is within a threshold percentage of the respective baseline authentication factor. In some examples, the number of authentication factors required for authentication may be defined by a remote officer. In some instances, the number may be defined by receiving an indication of a minimum number of authentication factors to be received by host 4. The authentication process may then additionally include determining that a majority of the received authentication factors are within the threshold percentage of the respective baseline authentication factor. In other instances, the number may be defined by receiving an indication of a number of authentication factors required to enable access to host 4. The authentication process may then additionally include determining that a number of received authentication factors is greater than or equal to the number of authentication factors required to enable access to the computing device.

Figure 2:
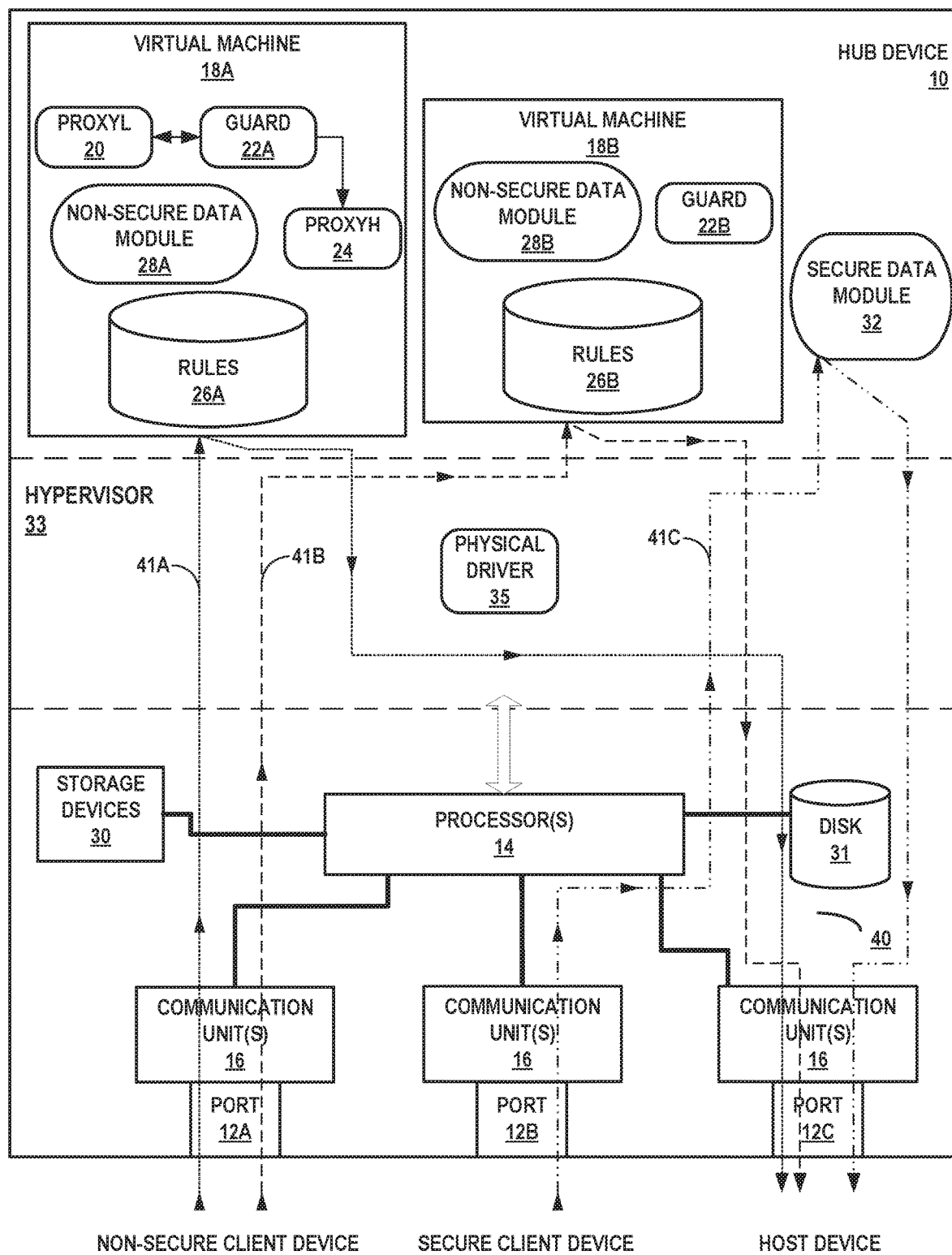
FIG. 2 is a block diagram illustrating an example hub device of FIG. 1 in more detail.

FIG. 2 is a block diagram illustrating a detailed example of hub device 10 configured to receive data packets from both secure client devices and non-secure client devices and to forward the received data packets to a host device, in accordance with one or more techniques of this disclosure. In the techniques of the current disclosure, the computing device that performs the authentication techniques described herein may receive the authentication factors from biometric authentication devices via a hub device, such as hub device 10. FIG. 2 illustrates some particular examples of hub 10, and many other examples of hub 10 may be used in other instances and may include a subset of the components included in example hub 10 or may include additional components not shown in FIG. 2.

For example, hub 10 may include a battery to provide power to the components of hub 10, or hub 10 may include more ports than three (e.g., four or more ports). Similarly, the components of hub 10 shown in FIG. 2 may not be necessary in every example of hub 10. For example, in some configurations, hub 10 may not include one or both of virtual machines 18A and 18B, meaning that only a single virtual machine may be included for handling data packets received from a non-secure source. However, for ease of illustration, hub 10 is shown in FIG. 2 to include both virtual machines 18A and 18B. As shown in the example of FIG. 2, hub 10 includes one or more processors 14, one or more communication units 16, virtual machines 18A and 18B executable by one or more processors 14, and one or more storage devices 30.

One or more storage devices 30 of hub 10 include virtual machines 18A and 18B and secure data module 32. One or more storage devices 30 may be configured to store information within hub 10 during operation. Storage device 30, in some examples, is described as a computer-readable storage medium. In some examples, storage device 30 is a temporary memory, meaning that a primary purpose of storage device 30 is not long-term storage. Storage device 30, in some examples, are described as volatile memories, meaning that storage device 30 does not maintain stored contents when the computing device is turned off. Examples of volatile memories include random access memories (RAM), dynamic random-access memories (DRAM), static random-access memories (SRAM), and other forms of volatile memories known in the art. In some examples, storage device 30 is used to store program instructions for execution by processors 14.

Storage devices 30, in some examples, also include one or more computer-readable storage media. Storage devices 30 may be configured to store larger amounts of information than volatile memory. Storage devices 30 may further be configured for long-term storage of information. In some examples, storage devices 30 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Disk 31 represents computer readable storage media that includes volatile and/or non-volatile, removable and/or non-removable media implemented in any method or technology for storage of information such as processor-readable instructions, data structures, program modules, or other data. Computer readable storage media includes, but is not limited to, random access memory (RAM), read-only memory (ROM), EEPROM, flash memory. CD-ROM, digital versatile discs (DVD) or other optical storage, magnetic cassettes, magnetic tape, magnetic disk storage or other magnetic storage devices, or any other medium that can be used to store the desired information and that can be accessed by processor 14.

Communication channels 40, represented by the solid lines in FIG. 2, may interconnect each of (or some subcombination of) the components 14, 16, 12A, 12B, 12C, and 30 for inter-component communications (physically, communicatively, and/or operatively). In some examples, communication channels 40 may include a system bus, a network connection, an inter-process communication data structure, or any other method for communicating data. The communication channels for a particular set of components may be isolated from another set of components.

Virtual data paths 41A-41C, represented by the dotted lines of various patterns, represent virtual connections within hub 10. For instance, data packets may be received by one of ports 12A-12C and be processed by one of virtual machines 18A-18B or secure data module 32. After being processed, the data packets may be output to a different device via another one of ports 12A-12C. Although each of virtual data paths 41A-41C is shown as being received by one of ports 12A or 12B and being output by port 12C, each of the data paths may be reversed. In other words, port 12C may receive data from the host device to be output to non-secure client devices or secure client devices via ports 12A or 12B.

One or more communication units 16 of hub 10 may communicate with external devices, such as a server device, a host device, secure client devices, and/or non-secure client devices, via one or more wired and/or wireless networks by transmitting and/or receiving network signals on the one or more networks. Communication units 16 may include a network interface card, such as an Ethernet card, an optical transceiver, a radio frequency transceiver, or any other type of device that can send and receive information. Examples of such network interfaces may include Bluetooth, infrared signaling, 3G, LTE, and Wi-Fi radios as well as Universal Serial Bus (USB) and Ethernet. In some examples, hub 10 utilizes communication units 16 to wirelessly communicate with another computing device that is operably coupled to hub 10, such as host device 4, secure client devices 6, and/or non-secure client devices 8 of FIG. 1.

In some examples, communication units 16 may include a sufficient number of communication units such that each of ports 12A-12C connects to components in hub 10 through a respective communication unit. In other words, port 12A may utilize a first one of communication units 16 to receive data packets from an outside computing device and to send the received data packets to the correct units for processing. In other examples, the respective ports 12A-12C may be configured to automatically send the received packets to the correct units on its own. In other words, communications channels for different sets of components can be isolated.

One or more processors 14, in one example, are configured to implement functionality and/or process instructions for execution within hub 10. For example, processors 14 may be capable of processing instructions stored in storage device 30. Examples of processors 14 may include, any one or more of a microprocessor, a controller, a digital signal processor (DSP), an application specific integrated circuit (ASIC), a field-programmable gate array (FPGA), or equivalent discrete or integrated logic circuitry.

Hub 10 executes a hypervisor 33 to manage virtual machines 18. Example hypervisors include Kernel-based Virtual Machine (KVM) for the Linux kernel, Xen, ESXi available from VMware, Windows Hyper-V available from Microsoft, and other open-source and proprietary hypervisors. Hypervisor 33 may represent a virtual machine manager (VMM). Hypervisor 33 includes a physical driver 35 to use the physical function provided by a network interface card.

Each of virtual machines 18 may include a virtual driver presented directly into the virtual machine guest operating system, effectively bypassing hypervisor 33 to offer direct communication between communication units 16 and the virtual machine. This may reduce hypervisor 33 overhead involved with software-based, vSwitch implementations.

Hub 10 may include virtual machines 18A and 18B (collectively, virtual machines 18), and secure data module 32. Each of virtual machines 18A and 18B may include a respective non-secure data module 28A and 28B. Modules 28A, 28B, and 32 may perform operations described using software, hardware, firmware, or a mixture of hardware, software, and firmware residing in and/or executing at hub 10. Hub 10 may execute modules 28A, 28B, and 32 with one or more processors. Hub 10 may execute modules 28A. 28B, and 32 as a virtual machine executing on underlying hardware. Modules 28A, 28B, and 32 may execute as a service or component of an operating system or computing platform. Modules 28A, 28B, and 32 may execute as one or more executable programs at an application layer of a computing platform. Modules 28A, 28B, and 32 may be otherwise arranged remotely to and remotely accessible to hub 10, for instance, as one or more network services operating at a network in a network cloud. In other words, modules 28A, 28B, and 32 may not be executing at hub 10. Instead, modules 28A, 28B, and 32 may be executing at a remote computing system (e.g., a server).

Virtual machines 18 and secure data module 32 may be stored in long-term storage, such as storage 30. However, when virtual machines 18 or secure data module 32 are executed by processor 14, processor 14 may read virtual machines 18 or secure data module 32 into volatile memory, such as disk 31. Virtual machines 18 or secure data module 32 may be stored in disk 31 throughout processor 14's execution of virtual machines 18 or secure data module 32.

Virtual machines 18 may be an emulation of a computer system. Virtual machines 18 may be based on computer architectures and provide functionality of a physical computer. Virtual machines 18 may be implemented in hub 10 using specialized hardware, software, or a combination thereof. Virtual machines 18 may be process virtual machines designed to execute the techniques described herein in a platform-independent environment. Specifically, each of virtual machines 18 may be designed to execute the guard and filtering techniques for data packets received from a non-secure client device. Although shown as virtual machines, virtual machines 18A and/or 18B may instead be containers. In such instances, a kernel of hypervisor 33 may allow for multiple, distinct virtualization engines that may enable the performance of the techniques described herein. Each of virtual machines 18A and 18B may include various hardware or software components to perform the techniques of this disclosure. These components are described in greater detail below.

In accordance with the techniques of this disclosure, processors 14 of hub 10 may receive, via port 12A, a first data packet from a non-secure client device. For example, the non-secure client device may be a UAV attempting to send data (e.g., a full motion video TCP stream) to the host device. The UAV may not be configured to operate in accordance with a trusted or secure protocol. However, the UAV may still generate information that would be beneficial to transmit to host 4. As such, the UAV may transmit the data packets associated with the TCP stream to hub 10 via port 12A. In examples where hub 10 includes virtual machine 18A, the first data packet may generally follow path 41A, i.e., the first data packet may be received by port 12A, analyzed using virtual machine 18A, and output via port 12C. In other examples where hub 10 includes virtual machine 18B, the first data packet may generally follow path 41B, i.e., the first data packet may be received by port 12A, analyzed using virtual machine 18B, and output via port 12C. In other examples, the first data packet may include an authentication factor from an authentication device that host 4 may use to determine an identity of a user of the authentication device.

Processors 14 of hub 10 may also receive, via port 12B, a second data packet from a secure client device. For instance, the secure client device may be a global positioning system (GPS) receiver device that transmits data packets that include various locations to hub 10 over a secure channel. Host 4 may request a status update from a user of the GPS with regards to the location of the GPS, and the GPS may respond by transmitting the data packets to hub 10 via port 12B. The second data packet, upon being received at port 12B, may generally follow path 41C within hub 10, i.e., the second data packet may be received by port 12B, analyzed using secure data module 32, and output via port 12C.

In some examples, based on the sender of the respective data packet, processor 14 may perform separate guard processes on the respective data packet. For instance, non-secure data modules 28A and/or 28B may receive the non-secure data packet from port 12A and perform a first guard process on the first data packet based on the security classification of the UAV (i.e., non-secure or untrusted) and secure data module 32 may perform a second guard process on the second data packet based on the security classification of the GPS (e.g., a secure security classification, such as secret, top secret, classified, or protected). For the second guard process, in some instances, secure data module 32 may simply forward the second data packet to the host device via port 12C. In other instances, for the second guard process, secure data module 32 may analyze contents of the second data packet to determine an identity of the sender of the second data packet or the type of contents in the second data packet prior to forwarding the second data packet to the host device via port 12C. As the second data packet may come from a secure and trusted client device, secure data module 32 may refrain from determining an integrity of the received data and performing a virus scan operation on the second data packet.

For the first guard process, non-secure data module 28A or 28B may execute the respective guard process 22A or 22B to perform an integrity check on the first data packet based at least in part on a type of connection between hub 10 and the non-secure client device and a data type of the first data packet. In other words, the data packet may have a different structure depending on the type of data stored within the data packet and the protocol used to transmit the data packet to hub 10. As such, the specific method for determining the integrity of the first data packet may vary based on the expected structure of the first data packet. Non-secure data module 28A or 28B may determine an expected structure of the first data packet based at least in part on type of connection between hub 10 and the non-secure client device and the data type of the first data packet. Non-secure data module 28A or 28B may also determine an actual structure of the first data packet and compare the actual structure with the expected structure. If non-secure data module 28A or 28B determines that the actual structure of the first data packet matches the expected structure of the first data packet, non-secure data module 28A or 28B may determine that the first data packet passes the integrity check and send the first data packet to the host device via port 12C. Conversely, if non-secure data module 28A or 28B determines that the actual structure of the first data packet does not match the expected structure of the first data packet, non-secure data module 28A or 28B may determine that the first data packet fails the integrity check and blocks the first data packet from reaching the host device.

Part of the integrity check may include non-secure data modules 28A and 28B determining that the actual structure of the first data packet matches an expected structure based on the type of data stored within the data packet and the protocol used to transmit the data packet to hub 10. For instance, if the UAV sends the TCP stream using Wi-Fi, non-secure data modules 28A and 28B may expect the first data packet to have a particular structure with particular bitfields filled out in particular ways. Non-secure data modules 28A and 28B may determine that the first data packet passes the integrity check if the bitfields match the expected structure.

Another part of the integrity check may include non-secure data modules 28A and 28B performing a virus scan operation on the first data packet. The virus scan operation may include comparing certain values within the data packet to known virus or malware structures. If non-secure data modules 28A and 28B determine that the first data packet contains a virus or malware, then non-secure data modules 28A and 28B may block the first data packet from reaching the host device. Conversely, if non-secure data modules 28A and 28B determines that the virus scan operation shows no harmful data in the first data packet, non-secure data modules 28A and 28B may forward the first data packet to the host device via port 12C.

Secure data module 32 and non-secure data modules 28A and 28B of hub 10 may send, via port 12C, the first data packet and the second data packet to the host device. The respective data modules may forward the respective data packets to host device 4 either upon receipt of the respective data packets or after the respective data packets have been processed. In other words, the respective data modules may not necessarily forward the first data packet and the second data packet simultaneously, but instead forward the first data packet and the second data packet after the respective data modules determines the respective data packet to be safe to forward to the host device in the respective data packet's own respective processing loop. The timing with which non-secure data modules 28A and/or 28B forward the first data packet is independent of the timing with which secure data module 32 forwards the second data packet.

In some examples, modules 28A, 28B, and 32 may simply forward the first data packet and the second data packet to the host device upon receiving the respective data packets. In other examples, as described above, modules 28A and 28B may implement some form of guard process to evaluate the first data packet received from the non-secure client device. Upon determining that the first data packet meets a threshold level of integrity, non-secure data modules 28A and 28B may forward the first data packet to the host device via port 12C. In still other instances, secure data module 32 may process certain information regarding the second data packet (e.g., sender information or content information) prior to forwarding the second data packet to the host device.

In some examples, non-secure data module 28A or 28B of hub 10 may receive an outgoing message to be sent to the non-secure client device. For instance, the host device may attempt to send an ACK message to the UAV. In some instances, non-secure data modules 28A and 28B of hub 10 may prevent all outgoing traffic from reaching non-secure client device 8A. In such examples, non-secure data module 28A or 28B of hub 10 may receive an outgoing message to be sent to the non-secure client device. Upon determining that the intended recipient of the outgoing message is a non-secure client device (e.g., the UAV), non-secure data module 28A or 28B of hub 10 may refrain from sending the outgoing message to the non-secure client device so as to protect the integrity of the secured system.

In other examples, hub 10 may forward the ACK message to the non-secure client device. Prior to forwarding the ACK message, non-secure data module 28A or 28B of hub 10 may scan the outgoing message to determine whether the outgoing message contains secure information that would be improper for a non-secure client device to receive based on various security protocols that hub 10 must operate within. In response to determining that the outgoing message does not contain secure information, non-secure data module 28A or 28B of hub 10 may send the outgoing message to the non-secure client device via port 12A. However, in response to determining that the outgoing message contains secure information, non-secure data module 28A or 28B of hub 10 may refrain from sending the outgoing message to the non-secure client device so as to protect the integrity of the secured system.

In some other examples, rather than waiting for the host device to produce and send ACK messages, virtual machine 18A may utilize proxy modules 20 and 24 to produce an ACK message. If non-secure data module 28A or 28B still receives the ACK message from the host device, guards 22A or 22B may block the received ACK message and utilize a proxy module to produce an ACK instead. For instance, if the first data packet was part of a TCP message, non-secure data module 28A may utilize the proxy modules 20 and 24, as described below, to create an ACK message and send the ACK message to the non-secure client device. By enabling hub 10 to create the ACK messages, outgoing communication from the host device to the non-secure client device is further limited or prevented. In creating a separate ACK message at ProxyL 20, hub 10 may maintain a one-way communication between the host device and the non-secure client device, as the non-secure client device will not receive any data created by the host device.

Depending on the final needs and requirements of the solution, both virtual machines 18A and 18B may be used as configurable options in addition to more or different types of flow controls. In the example of FIG. 2, virtual machine 18A uses two proxies 20 and 24, a high-side Proxy (e.g., ProxyH 24, or a proxy module located on the host-side of guard 22A) and a low-side proxy (e.g., ProxyL 20, or a proxy module located on the client-side (or low side) of guard 22A). Non-secure data module 28A may execute each of these proxies 20 and 24 to mimic or block the reverse packet flow in a TCP connection when no high to low traffic is required. A TCP application on the low side may expect ACKs and various feedback, including handshaking information, from the ultimate host device. ProxyL 20 may mimic or create these ACK messages as if ProxyL 20 were the actual endpoint, thus completing the data exchange loop needed for a full TCP connection. The TCP packets are then wrapped or modified to be user diagram protocol (UDP) packets and sent into the guard process where the flow is validated according to the configured flow type rules. Guard 22A may execute a guard process before ProxyL 20 handles the TCP connection. ProxyH 24 receives the ACKs and various TCP feedback and drops all traffic. ProxyH 24 may also receive the UDP packets from guard 22A and convert the UDP packets into TCP packets to forward on to an app on the host device.

Virtual machine 18B shows a simpler filtering technique that only includes guard 22B and does not mimic the TCP ACKs. In this example, traffic may flow both from the non-secure client device to the host device and from the host device to the non-secure client device. As such, the host device may generate the TCP ACK messages, which hub 10 may forward to the non-secure client device. Guard 22B may implement the same or more virus detection, deep packet inspection and other safeguards guard 22A.

In some examples, the cross-domain system in FIG. 2 may be implemented with or without virtual machines 18A and 18B. Virtual machines 18 may isolate the "low" traffic and "low" network interfaces from the rest of hub 10. However, other implementations of the functionality of each of virtual machines 18 may be utilized to perform the techniques of this disclosure.

Figure 3:
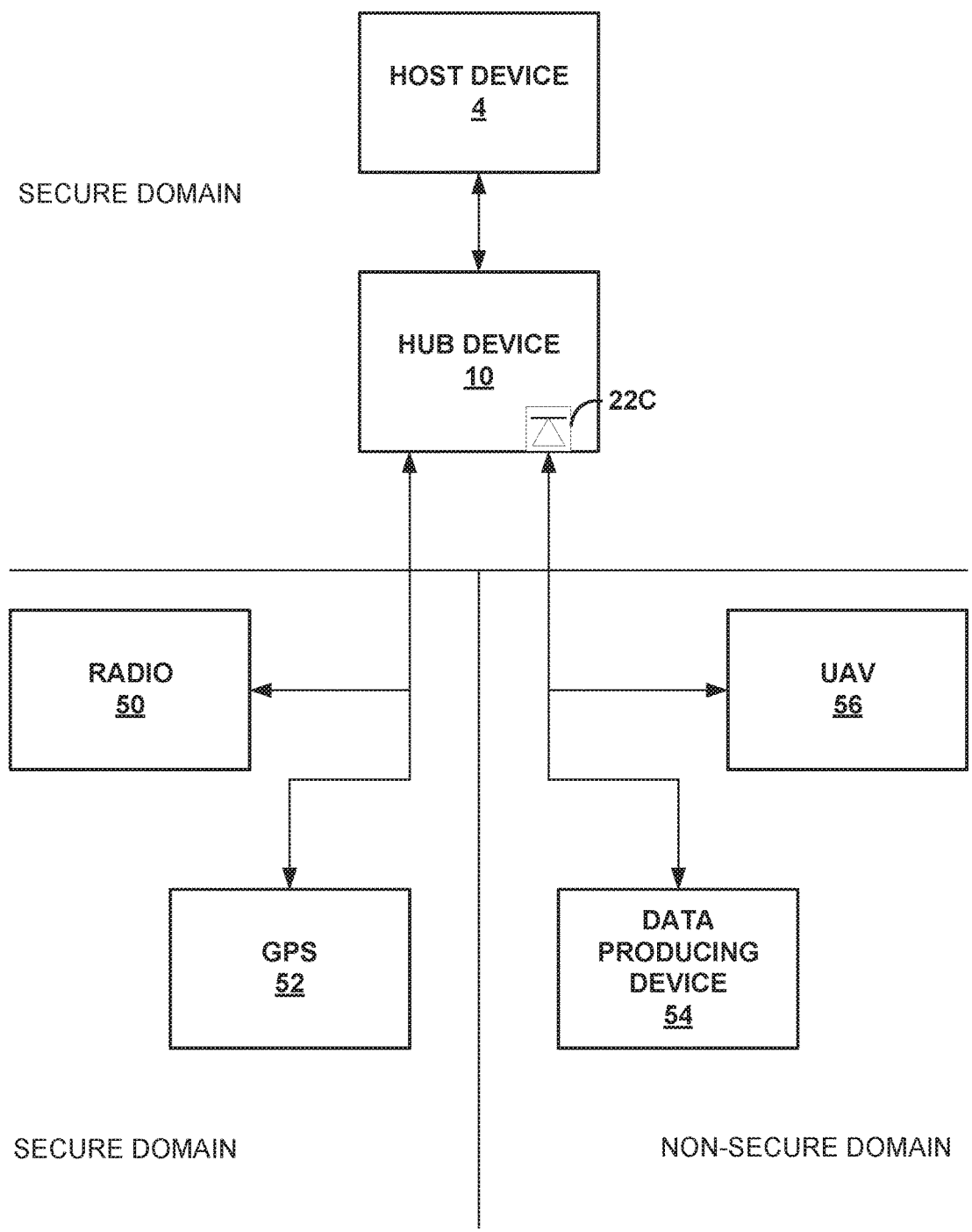
FIG. 3 is a block diagram illustrating an example system that includes a hub device configured to block outgoing communications to the non-secure client devices, in accordance with one or more techniques of this disclosure.

FIG. 3 is a block diagram illustrating an example system that includes hub device 10 configured to receive data packets from both secure client devices 50 and 52 and non-secure client devices 54 and 56, forward the received data packets to host device 4, and block outgoing communications to non-secure client devices 54 and 56, in accordance with one or more techniques of this disclosure. The techniques of FIG. 3 may be performed by one or more processors of a computing device, such as hub 10 illustrated in FIG. 1 and/or FIG. 2. For purposes of illustration only, the techniques of FIG. 3 are described within the context of hub 10 of FIG. 1, although computing devices having configurations different than that of hub 10 may perform the techniques of FIG. 3.

One option for controlling the outgoing traffic to non-secured client devices 54 and 56 is for guard 22C (similar to guards 22A and 22B of FIG. 2) in hub 10 to control the outgoing traffic from hub 10 to non-secured client devices 54 and 56. In this option, guard 22C may be implemented as part of hub 10 or operably connected to hub 10 and may allow general traffic to flow in only one direction (i.e., from the non-secure client devices 54 and 56 to hub device 10). In one instance, the data flow being in only one direction is absolute and all outgoing data from hub device 10 to non-secure client devices 54 and 56 is blocked at guard 22C. However, this absolute block may break TCP network protocols and other protocols that require small ACK or acknowledgment packets to flow back to data producing device 54 and UAV 56. In another instance, guard 22C may utilize dynamic filtering options for one-way packet filtering with ACKs going back to the sender (e.g., data producing device 54 and UAV 56). In this instance, guard 22C may be involved with more processing and may have more dynamic capabilities. In the example of FIG. 3, guard 22C may be configured to monitor and control the outgoing traffic to non-secure client devices 54 and 56 universally, needing only the single guard 22C to monitor and control the outgoing traffic regardless of the connection type or the device type of the ultimate non-secure client device 54 and 56.

Contrast this with the "bump-in-the-wire" approach. In this option, guard 22C would be implemented as a respective intermediary on each of the connections between non-secured client devices 54 and 56 and hub 10 to allow traffic to flow in only one direction (i.e., from the non-secure client devices 54 and 56 to hub device 10). Each of the guards would need to be configured independently, as there may not be a common interface for network devices 58A and 58B. Further, a separate guard would be needed for each and every potential connection with a non-secure client device, further increasing the complexity and variability of the overall system.

Another contrasting example to the example of FIG. 3 is to install a separate device (i.e., a cross-domain guard) inline between non-secure client devices 54 and 56 and hub 10. The cross-domain guard may apply the one-way filtering techniques of allowing TCP ACK packets to flow from hub 10 to data producing device 54 and UAV 56 to provide the packet filtering for one-way communication with limited acknowledgement capability. However, each non-secure client device 54 and 56 would still need a respective cross-domain guard device, and each cross-domain guard device may have to be configured independently. Further, a separate cross-domain guard would be needed for each and every potential connection with a non-secure client device, further increasing the complexity and variability of the overall system.

Figure 4:
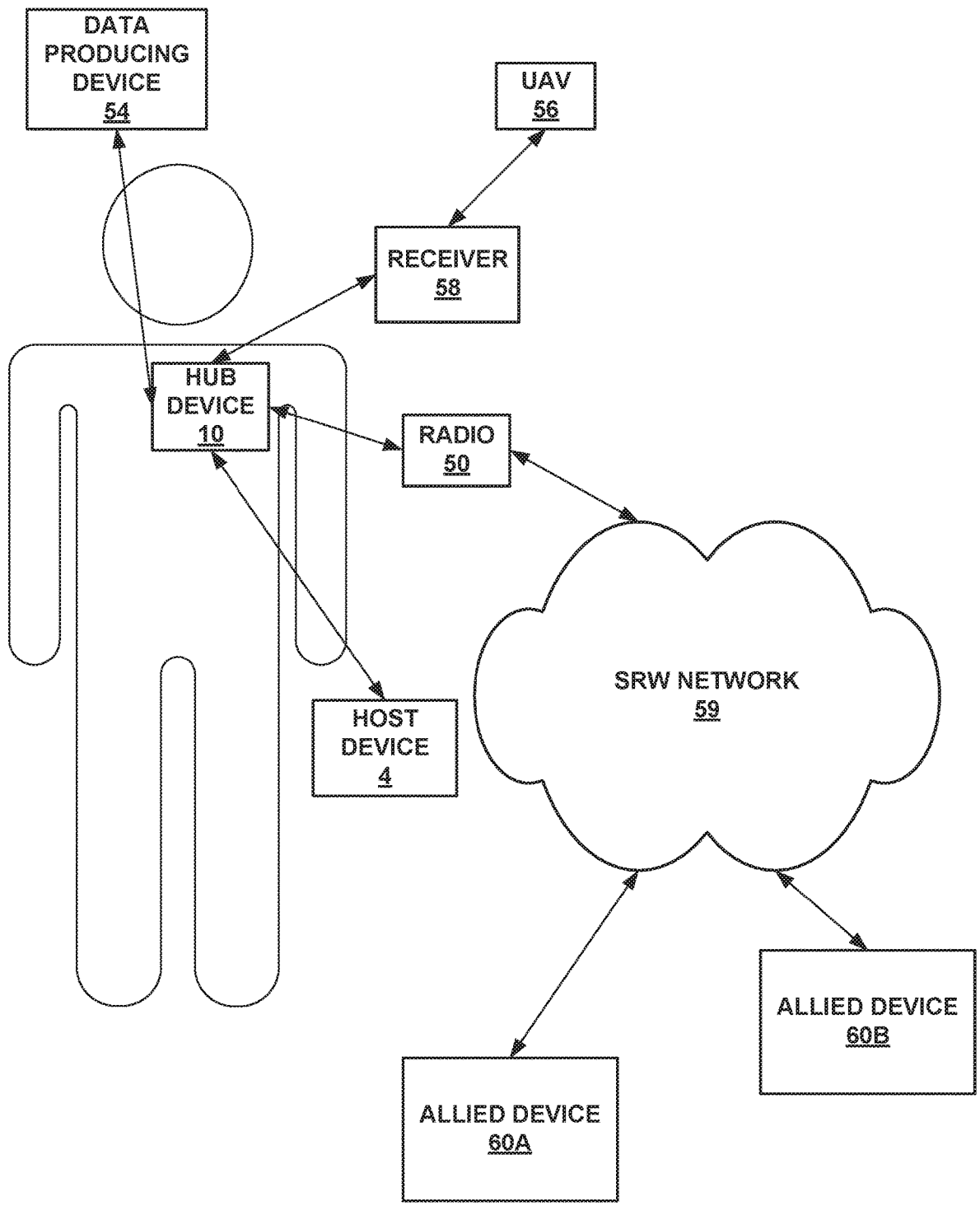
FIG. 4 is a block diagram illustrating an example system that includes a wearable hub device, in accordance with one or more aspects of this disclosure.

FIG. 4 is a block diagram illustrating an example system that includes a wearable hub device 10, in accordance with one or more aspects of this disclosure. The techniques of FIG. 4 may be performed by one or more processors of a computing device, such as hub 10 illustrated in FIG. 1 and/or FIG. 2. For purposes of illustration only, the techniques of FIG. 4 are described within the context of hub 10 of FIG. 1, although computing devices having configurations different than that of hub 10 may perform the techniques of FIG. 4.

In the example of FIG. 4, hub 10 may be connected to non-secured data producing device 54 and receiver 58, which receives information from non-secured UAV 56. Hub 10 is further connected to secured radio 50, which receives communications from allied devices 60A and 60B over a radio network (such as secure radio network 59), which may be a secured network. Since hub 10 is a wearable device, hub 10 may be used by soldiers in the field. Rather than only connecting a single device to host device 4 at any given time, hub 10 may enable multiple devices, both secured and non-secured, to connect to host 4 simultaneously, greatly increasing the efficiency of various operations that the soldier in the field may be tasked with performing.

Figure 5:
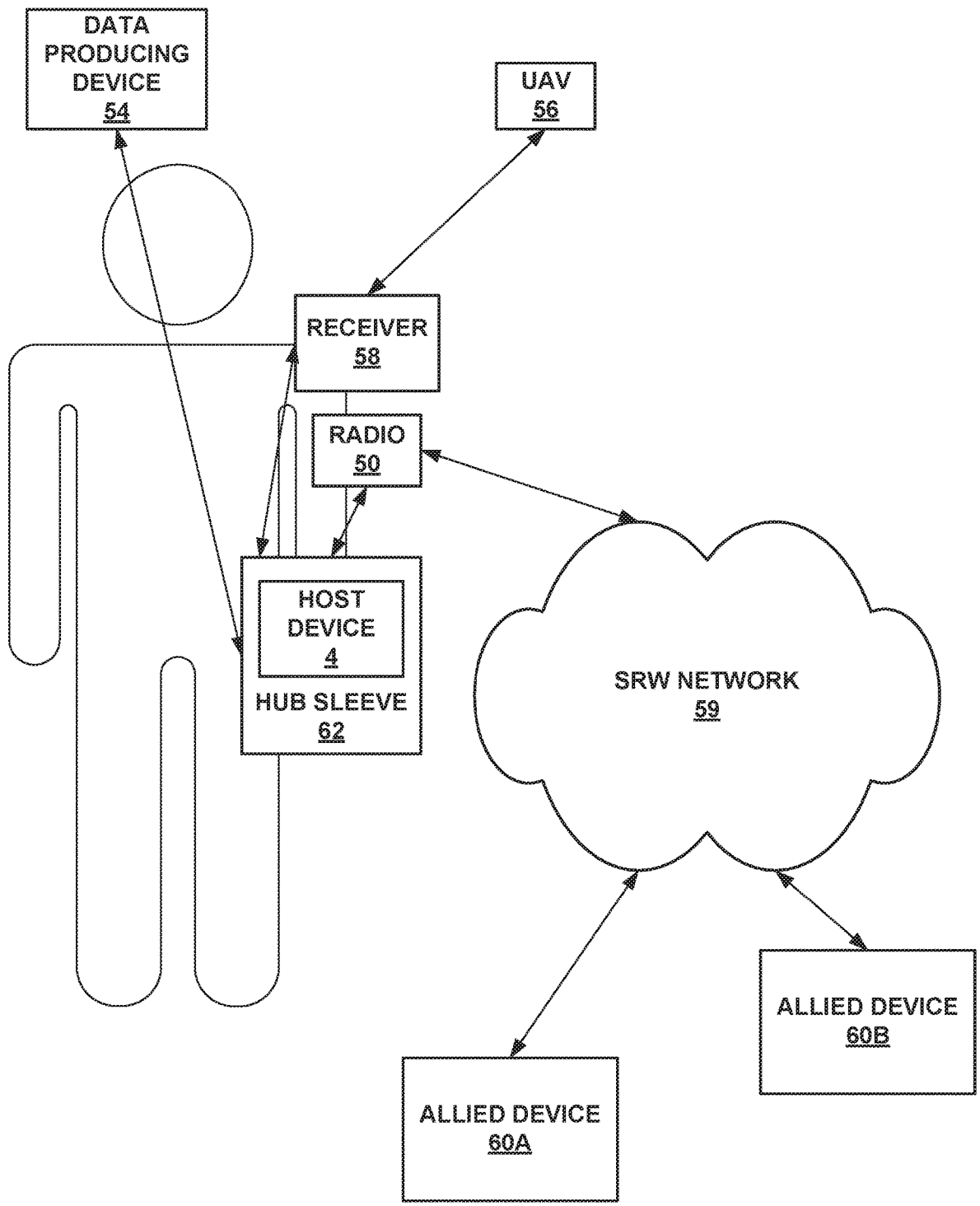
FIG. 5 is a block diagram illustrating an example system that includes a wearable hub device in the form of a sleeve around the host device, in accordance with one or more aspects of this disclosure.

FIG. 5 is a block diagram illustrating an example system that includes a wearable hub device in the form of hub sleeve 62 around host device 4, in accordance with one or more aspects of this disclosure. The techniques of FIG. 5 may be performed by hub sleeve 62, which may have similar functionalities to hub 10 illustrated in FIG. 1 and/or FIG. 2.

Hub sleeve 62 may generally include any mechanism for attaching a hub device, such as hub 10, to the body, clothing, or uniform of a user, or to host 4 itself. Hub sleeve 62 may also include an external CPU that may connect to host 4 rather than hub 10, which is a separate device. However, hub sleeve 62 may still perform the same functions of hub 10, including connecting to multiple devices, both secured and non-secured, and perform particular guard processes on the received non-secured data packets, in accordance with the techniques described throughout this disclosure.

In the example of FIG. 5, hub sleeve 62 may be connected to non-secured data producing device 54 and receiver 58, which receives information from non-secured UAV 56. Hub sleeve 62 is further connected to secured radio 50, which receives communications from allied devices 60A and 60B over secure radio network 59, which may be a secured network. Since hub sleeve 62 is a wearable device that is attached to host 4, hub sleeve 62 may be used by soldiers in the field. Rather than only connecting a single device to host 4 at any given time, hub sleeve 62 may enable multiple devices, both secured and non-secured, to connect to host 4 simultaneously, greatly increasing the efficiency of various operations that the soldier in the field may be tasked with performing.

Figure 6:
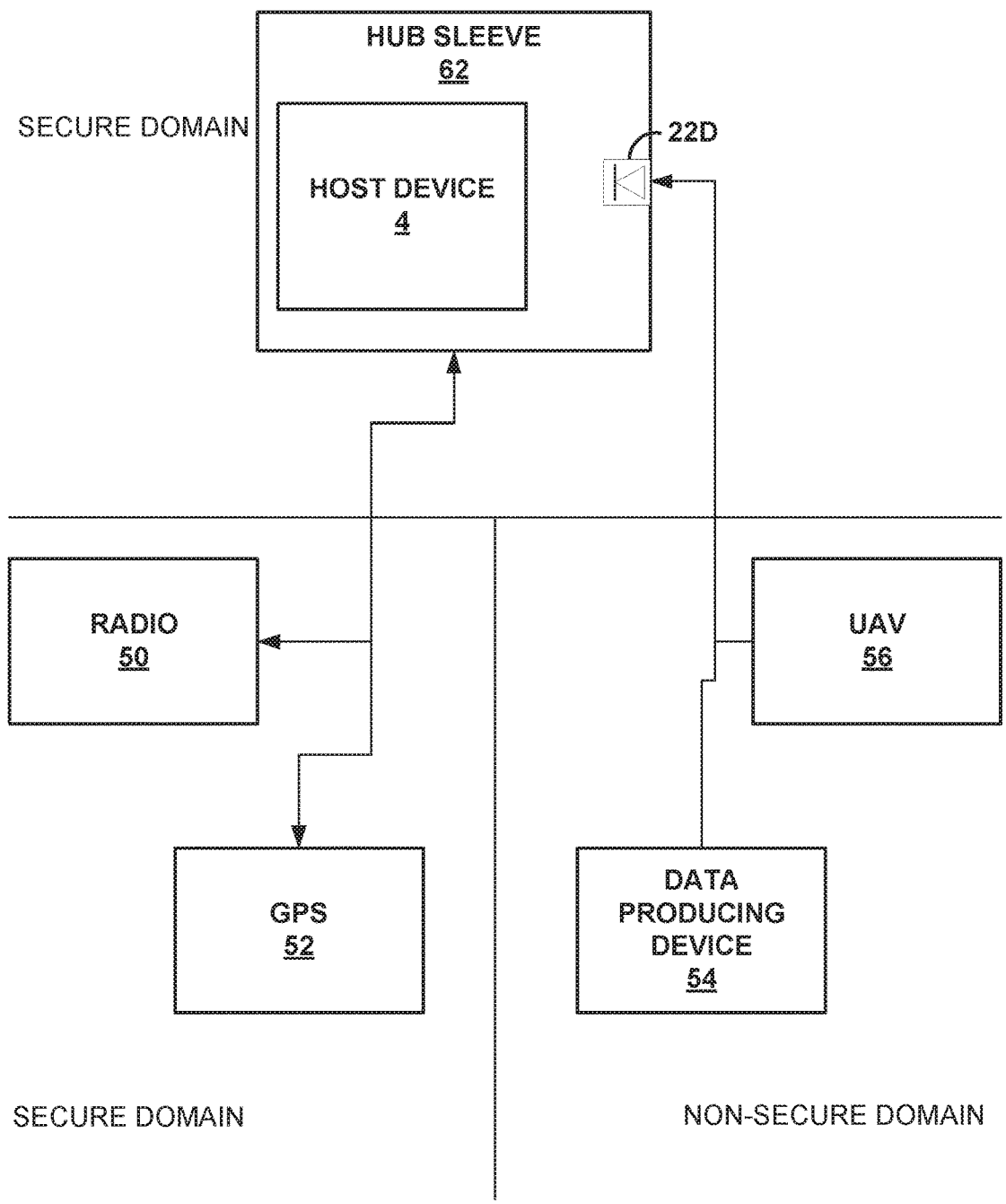
FIG. 6 is a block diagram illustrating an example system that includes a hub device in the form of a sleeve around the host device, in accordance with one or more aspects of this disclosure.

FIG. 6 is a block diagram illustrating an example system that includes hub sleeve 62 configured to receive data packets from secure client devices 50 and 52 and forward the received data packets to a host device 4. Hub sleeve 62, which is attached to host device 4, is further configured to receive data packets from non-secure client devices 54 and 56 and control outgoing communications to the non-secure client devices 54 and 56, in accordance with one or more aspects of this disclosure. For instance, hub sleeve 62 includes one-way guard port 22D, which restricts outgoing messages from going to UAV 56 and/or data producing device 54. The techniques of FIG. 6 may be performed by one or more processors of a computing device, such as hub 10 illustrated in FIG. 1 and/or FIG. 2. For purposes of illustration only, the techniques of FIG. 6 are described within the context of hub 10 of FIG. 1, although computing devices having configurations different than that of hub 10 may perform the techniques of FIG. 6.

In another example, the guard functionalities may be implemented in an advanced CPU within hub sleeve 62 operably connected to host device 4. In such an example, hub sleeve 62 may add more ports to host device 4 and may enable host device 4 to have a fully capable dual stack. As such, the functionality of hub device 10 may be split between hub device 10 and hub sleeve 62. Hub device 10 may process all data packets coming from devices 50 and 52 in the secure domain, and hub sleeve 62 may process all data packets coming from devices 54 and 56 in the non-secure domain.

Figure 7:
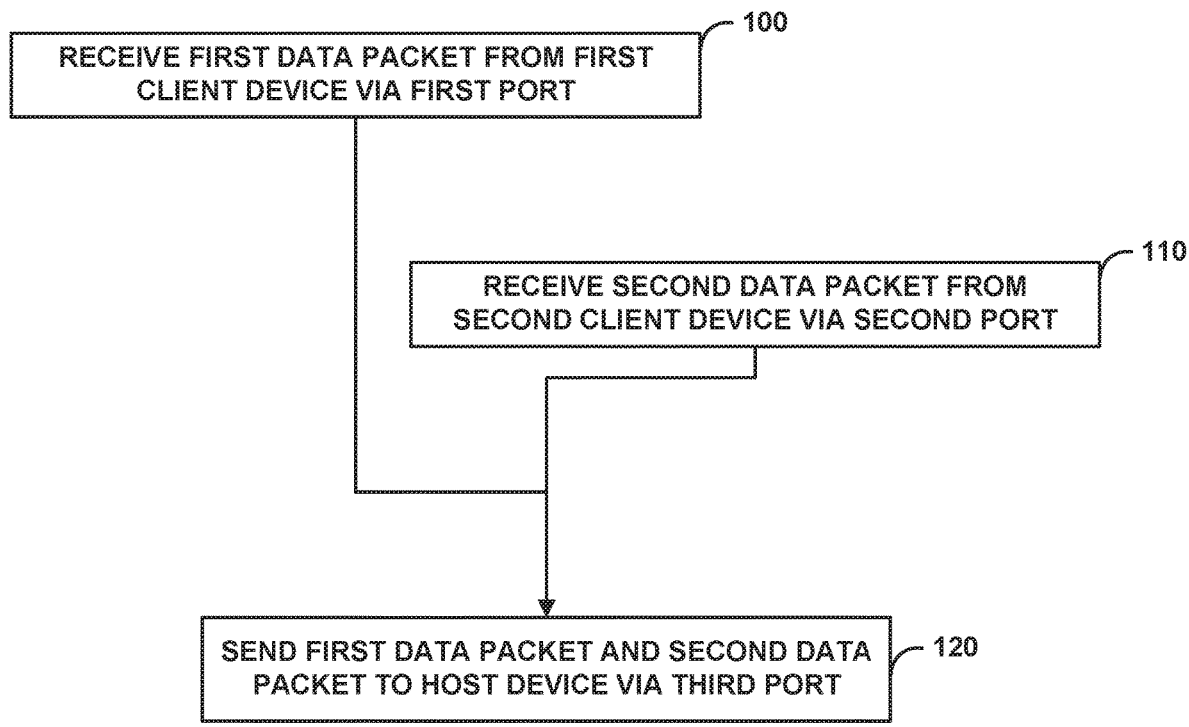
FIG. 7 is a flow diagram illustrating example operations of a hub device that implements data processing techniques in accordance with one or more aspects of this disclosure.

FIG. 7 is a flow diagram illustrating example operations of a hub device that implements data processing techniques in accordance with one or more aspects of this disclosure. The techniques of FIG. 7 may be performed by one or more processors of a computing device, such as hub 10 illustrated in FIG. 1 and/or FIG. 2. For purposes of illustration only, the techniques of FIG. 7 are described within the context of hub 10 of FIG. 1, although computing devices having configurations different than that of hub 10 may perform the techniques of FIG. 7. While the techniques described below with respect to FIG. 7 are described as being performed by processors 14, processors 14 may utilize other modules or applications, such as a virtual machine, to perform all or a portion of the techniques described herein, so as to maintain integrity between the secured data packets and the non-secured data packets.

In accordance with the techniques of this disclosure, processors 14 of hub 10 may receive, via port 12A, a first data packet from non-secure client device 8A (100). Processors 14 of hub 10 may also receive, via port 12B, a second data packet from secure client device 6A (110).

In some examples, based on the sender of the respective data packet, processor 14 may perform separate guard processes on the respective data packet. For instance, processors 14 may execute a separate virtual machine in hub 10, with the virtual machine performing a first guard process on the first data packet based on the security classification of non-secure client device 8A (i.e., non-secure or untrusted) and a second virtual machine performing a second guard process on the second data packet based on the security classification of secure client device 6A (e.g., a secure security classification, such as secret, top secret, classified, or protected). For the second guard process, in some instances, processors 14 may simply forward the second data packet to host 4 via port 12C. In other instances, for the second guard process, processors 14 may analyze contents of the second data packet to determine an identity of the sender of the second data packet or the type of contents in the second data packet prior to forwarding the second data packet to host 4 via port 12C. As the second data packet may come from a secure and trusted client device, processors 14 may refrain from determining an integrity of the received data and performing a virus scan operation on the second data packet.

For the first guard process, processors 14 of hub 10 may utilize the separate virtual machine to determine an integrity of the first data packet based at least in part on a type of connection between hub 10 and non-secure client device 8A and a data type of the first data packet. In other words, the data packet may have a different structure depending on the type of data stored within the data packet and the protocol used to transmit the data packet to hub 10. As such, the specific method for determining the integrity of the first data packet may vary based on the expected structure of the first data packet. If the virtual machine determines that the integrity of the first data packet is above a threshold integrity level, processors 14 may send the first data packet to host 4 via port 12C.

Part of the integrity check may include processors 14 utilizing the separate virtual machine to determine that the actual structure of the first data packet matches an expected structure based on the type of data stored within the data packet and the protocol used to transmit the data packet to hub 10. For instance, if non-secure client device 8A sends an image file over a USB connection, hub 10 may expect the first data packet to have a particular structure with particular bitfields filled out in particular ways. The virtual machine may determine that the first data packet passes the integrity check if the bitfields match the expected structure.

Another part of the integrity check may include processors 14 utilizing the separate virtual machine to perform a virus scan operation on the first data packet. The virus scan operation may include comparing certain values within the data packet to known virus or malware structures. If the virtual machine determines that the first data packet contains a virus or malware, then processors 14 may block the first data packet from reaching host 4. Conversely, if processors 14 determines that the virus scan operation shows no harmful data in the first data packet, processors 14 may forward the first data packet to host 4 via port 12C.

Processors 14 of hub 10 may send, via port 12C, the first data packet and the second data packet to host 4 (120). Port 12C may forward the respective data packets to host 4 either upon receipt of the respective data packets or after the respective data packets have been processed. In other words, port 12C may not necessarily forward the first data packet and the second data packet simultaneously, but instead forward the first data packet and the second data packet after processors 14 determines the respective data packet to be safe to forward to host 4 in the respective data packet's own respective processing loop. The timing with which processors 14 forward the first data packet is independent of the timing with which processors 14 forward the second data packet.

In some examples, processors 14 may simply forward the first data packet and the second data packet to host 4 upon receiving the respective data packets. In other examples, as described above, processors 14 may implement some form of guard process to evaluate the first data packet received from non-secure client device 8A. Upon determining that the first data packet meets a threshold level of integrity, processors 14 may forward the first data packet to host 4 via port 12C. In still other instances, processors 14 may process certain information regarding the second data packet (i.e., sender information or content information) prior to forwarding the second data packet to host 4.

In some examples, processors 14 of hub 10 may receive an outgoing message to be sent to non-secure client device 8A. For instance, host 4 may attempt to send an ACK message to non-secure client device 8A. Prior to forwarding the ACK message, processors 14 of hub 10 may scan the outgoing message to determine whether the outgoing message contains secure information that would be improper for a non-secure client device to receive. In response to determining that the outgoing message does not contain secure information, processors 14 of hub 10 may send the outgoing message to non-secure client device 8A via port 12A. However, in response to determining that the outgoing message contains secure information, processors 14 of hub 10 may refrain from sending the outgoing message to non-secure client device 8A so as to protect the integrity of the secured system.

In some other examples, rather than expecting host 4 to produce and send ACK messages, processors 14 may utilize a proxy module to produce an ACK message. For instance, if the first data packet was part of a TCP message, processors 14 may utilize the proxy module to create an ACK message and send the ACK message to non-secure client device 8A.

In other examples, processors 14 of hub 10 may prevent all outgoing traffic from reaching non-secure client device 8A. In such examples, processors 14 of hub 10 may receive an outgoing message to be sent to non-secure client device 8A. Upon determining that the intended recipient of the outgoing message is a non-secure client device (i.e., non-secure client device 8A), processors 14 of hub 10 may refrain from sending the outgoing message to non-secure client device 8A so as to protect the integrity of the secured system.

Figure 8:
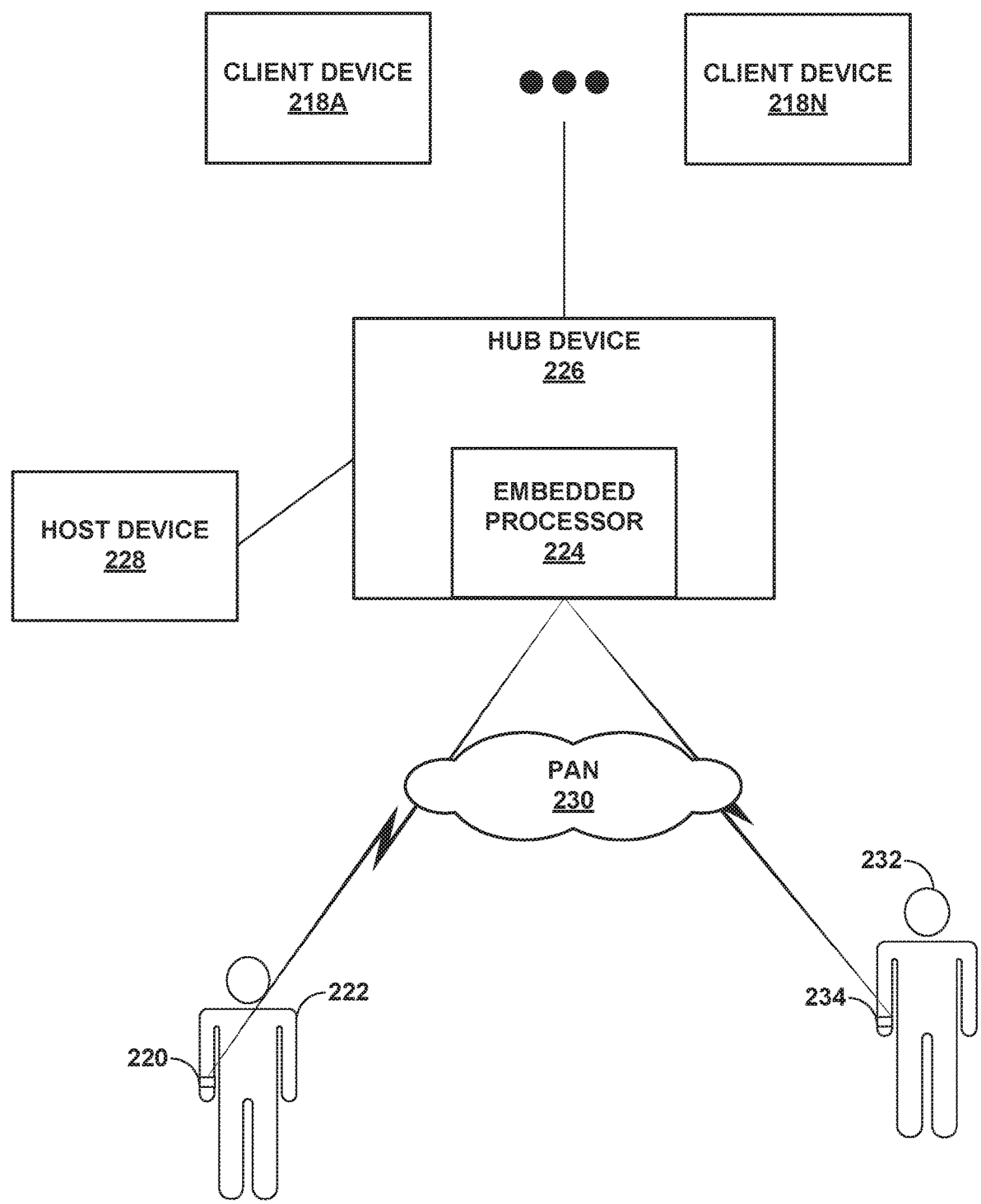
FIG. 8 is a block diagram illustrating an example authentication architecture in accordance with one or more aspects of this disclosure.

FIG. 8 is a block diagram illustrating an example authentication architecture in accordance with one or more aspects of this disclosure. In the example of FIG. 8, biometric authentication device 220 may receive input from user 222 to determine a respective authentication factor for user 222 (e.g., a biometric signature or biometric information). Host device 228 (which may be similar to host device 4 of FIG. 1) may receive, via hub device 226 (which may be similar to hub device 10 or hub sleeve 62 of FIGS. 1-7) and personal area network (PAN) 230, an authentication factor from biometric authentication devices 220 and determine whether user 222 is a particular trusted user of the devices in the tactical network. Host device 228, based on the results of the authentication process, may either grant or deny user 222 access to host device 228 and/or one or more client devices 218A-218N.

PAN 230 may be any local network over which devices (e.g., authentication devices 220 and hub device 226) may communicate over short distances. PAN 230 may be configured to carry data packets between these devices in accordance with any suitable protocol, including Bluetooth, Wi-Fi, and RFID.

An example of biometric authentication device 220 referred to throughout this disclosure are physiological sensors. The physiological sensors may be any sensor, attached to or otherwise carried by a user, that may detect something that the respective user has, something that the respective user is, or something that the respective user knows. For instance, authentication devices 220 may include one or more of a voice recognition sensor, an eye sensor (e.g., to perform an iris/retinal scan), a facial recognition sensor, a motion sensor, a hand geometry sensor, a hand grip sensor, a fingerprint sensor, an electrocardiogram (ECG) sensor, an ear print sensor, or a gait sensor. Biometric authentication device 220 may produce one or more of a voice pattern, a retinal scan, a facial recognition scan, a motion gesture, a hand geometry reading, a hand grip reading, a fingerprint, an electrocardiogram (ECG), an ear print, or a gait measurement.

Embedded processor 224, in one example, is configured to implement functionality and/or process instructions for execution within hub device 226. For example, embedded processor 224 may be capable of processing instructions stored in hub device 224. Examples of embedded processor 224 may include, any one or more of a microprocessor, a controller, a digital signal processor (DSP), an application specific integrated circuit (ASIC), a field-programmable gate array (FPGA), or equivalent discrete or integrated logic circuitry. Embedded processor 224 may also store and execute instructions or modules, such as a software-based data diode, that enable embedded processor to receive authentication factors from authentication devices 220 over PAN 230, either wirelessly or through a wired connection. By only letting data travel from authentication devices 220 to embedded processor 224 and then to host device 228, and by ensuring that no data can traverse the opposite path, the techniques described herein provide a way to incorporate low-cost authentication devices for fast user authentication in a secure fashion.

The techniques described herein analyze a biometric authentication factor to determine how many successfully verified factors are required to grant user access to host device 228. Ultimately, the techniques described herein grant legitimate users immediate access to the EUD (e.g., host device 228), with little or no additional effort.

In the example of FIG. 8, user 222 may be attempting to access data on host device 228 in order to treat a medical ailment of user 232. Biometric authentication device 220 may read data from various respective sensors (e.g., a voice pattern, a finger tap sequence, a retinal scan, a motion gesture, a hand geometry reading, a hand grip reading, a fingerprint, an electrocardiogram (ECG), an ear print, a radio frequency identification tag, a gait measurement, and/or other authentication signals) to generate an authentication factor for user 222. Biometric authentication device 220 may transmit the authentication factor to embedded processor 224 of hub device 226 via PAN 230, which forwards the authentication factor to host device 228 upon ensuring the integrity of the authentication factors. Host device 228 may analyze the authentication factor to determine if the authentication factor indicates that user 222 is a particular trusted user. If the validation does not indicate that user 222 is the particular trusted user, then host device 228 may determine that it may be compromised and can recheck and initiate protocols and policies in response.

Once host device 228 confirms that user 222 is a trusted user, host device may determine that user 222 has medic credentials based on information in a user information database. Using these credentials, host device 228 may enable user 222 access to medical information for other users in the vicinity of user 222. For instance, user 232 may require medical attention, and user 232 may be wearing biometric authentication device 234 (similar to biometric authentication device 220). Biometric authentication device 234 may read data from various respective sensors (e.g., a voice pattern, a finger tap sequence, a retinal scan, a motion gesture, a hand geometry reading, a hand grip reading, a fingerprint, an electrocardiogram (ECG), an ear print, a radio frequency identification tag, a gait measurement, and/or other authentication signals) to generate an authentication factor for user 232. Biometric authentication device 234 may transmit the authentication factor to embedded processor 224 of hub device 226 via PAN 230, which forwards the authentication factor to host device 228 upon ensuring the integrity of the authentication factors. Host device 228 may analyze the authentication factor to determine an identity of user 232 and retrieve medical information for user 232. Host device 228 may display the medical information for review by user 222, enabling user 222 to provide precise and effective medical care to user 232 in a physical location where access to a full medical history may be difficult.

Figure 9:
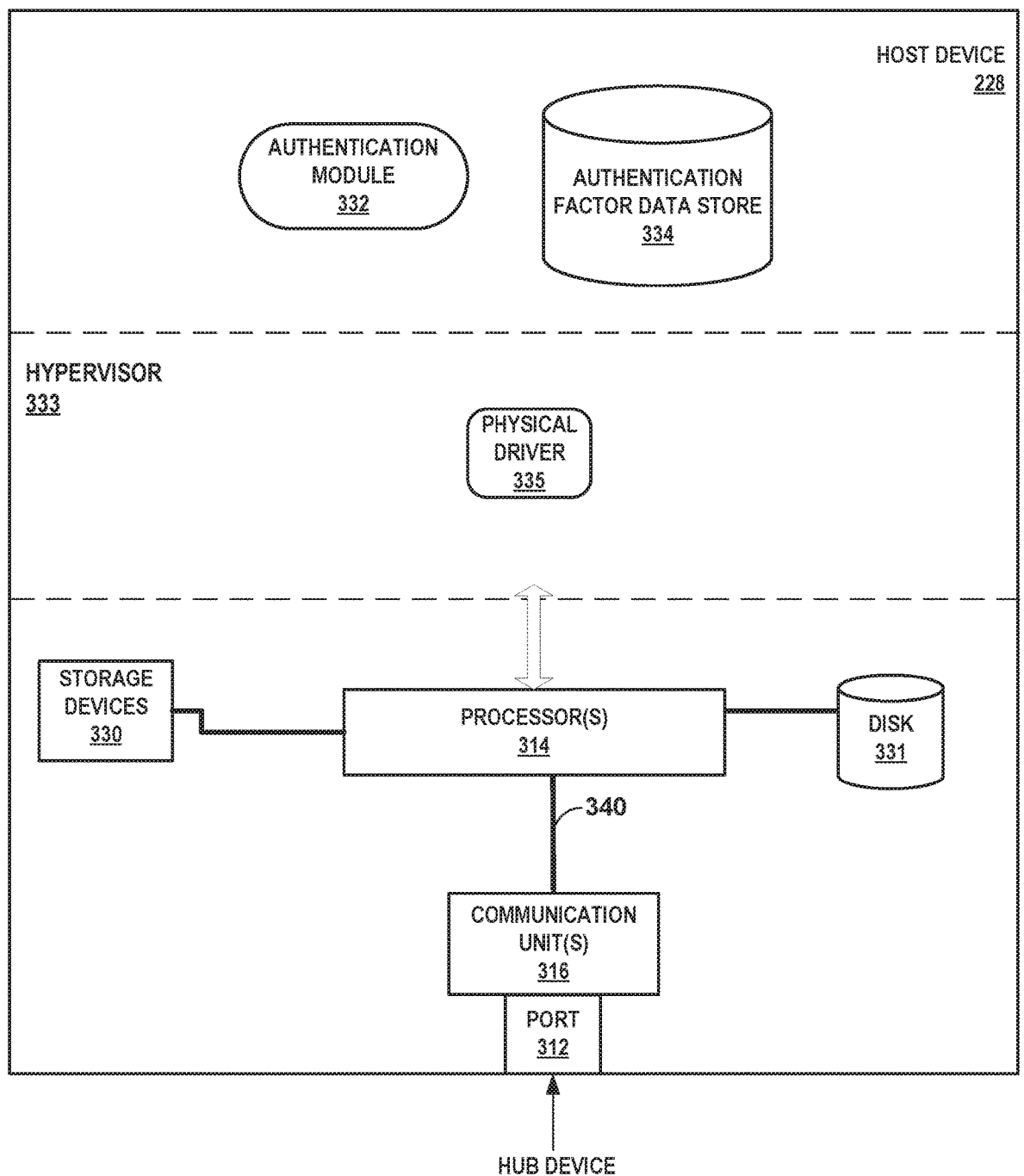
FIG. 9 is a block diagram illustrating an example computing device of FIG. 8 in more detail.

FIG. 9 is a block diagram illustrating a detailed example of host device 228 configured to receive authorization factors from authentication devices and to analyze the authentication factors to determine the identity of a potential user of a client device, in accordance with one or more techniques of this disclosure. FIG. 9 illustrates some particular examples of host device 228, and many other examples of host device 228 may be used in other instances and may include a subset of the components included in example host device 228 or may include additional components not shown in FIG. 9.

For example, host device 228 may include a battery to provide power to the components of host device 228, or host device 228 may include more ports than three (e.g., four or more ports). Similarly, the components of host device 228 shown in FIG. 2 may not be necessary in every example of host device 228. For example, in some configurations, host device 228 may not include authentication module 332 and may instead include a virtual machine that performs the same functions as authentication module 332. As shown in the example of FIG. 9, host device 228 includes one or more processors 314, one or more communication units 316, authentication module 332 executable by one or more processors 314, and one or more storage devices 330.

One or more storage devices 330 of host device 228 include authentication module 332 and authentication factor data store 334. One or more storage devices 330 may be configured to store information within host device 228 during operation. Storage device 330, in some examples, is described as a computer-readable storage medium. In some examples, storage device 330 is a temporary memory, meaning that a primary purpose of storage device 330 is not long-term storage. Storage device 330, in some examples, is described as volatile memories, meaning that storage device 330 does not maintain stored contents when the computing device is turned off. Examples of volatile memories include RAM, DRAM, SRAM, and other forms of volatile memories known in the art. In some examples, storage device 330 is used to store program instructions for execution by processors 314.

Storage devices 330, in some examples, also include one or more computer-readable storage media Storage devices 330 may be configured to store larger amounts of information than volatile memory. Storage devices 330 may further be configured for long-term storage of information. In some examples, storage devices 330 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Disk 331 represents computer readable storage media that includes volatile and/or non-volatile, removable and/or non-removable media implemented in any method or technology for storage of information such as processor-readable instructions, data structures, program modules, or other data. Computer readable storage media includes, but is not limited to, random access memory (RAM), read-only memory (ROM), EEPROM, flash memory, CD-ROM, digital versatile discs (DVD) or other optical storage, magnetic cassettes, magnetic tape, magnetic disk storage or other magnetic storage devices, or any other medium that can be used to store the desired information and that can be accessed by processor 314.

Communication channels 340, represented by the solid lines in FIG. 9, may interconnect each of (or some subcombination of) the components 314, 316, 312, and 330 for inter-component communications (physically, communicatively, and/or operatively). In some examples, communication channels 340 may include a system bus, a network connection, an inter-process communication data structure, or any other method for communicating data. The communication channels for a particular set of components may be isolated from another set of components.

One or more communication units 316 of host device 228 may communicate with external devices, such as a server device, a client device, secure client devices, and/or non-secure client devices, via one or more wired and/or wireless networks by transmitting and/or receiving network signals on the one or more networks. Communication units 316 may include a network interface card, such as an Ethernet card, an optical transceiver, a radio frequency transceiver, or any other type of device that can send and receive information. Examples of such network interfaces may include Bluetooth, infrared signaling, 3G, LTE, and Wi-Fi radios as well as Universal Serial Bus (USB) and Ethernet. In some examples, host device 228 utilizes communication units 316 to wirelessly communicate with another computing device that is operably coupled to host device 228, such as physiological sensors 218 of FIG. 8.

Port 312 may utilize a first one of communication units 316 to receive data packets from an outside computing device and to send the received data packets to the correct units for processing. In other examples, the port 312 may be configured to automatically send the received packets to the correct units on its own. In other words, communications channels for different sets of components can be isolated.

One or more processors 314, in one example, are configured to implement functionality and/or process instructions for execution within host device 228. For example, processors 314 may be capable of processing instructions stored in storage device 330. Examples of processors 314 may include, any one or more of a microprocessor, a controller, DSP, an ASIC, an FPGA, or equivalent discrete or integrated logic circuitry.

In instances where authentication module 332 is a virtual machine, host device 228 executes a hypervisor 333 to manage the virtual machines. Example hypervisors include Kernel-based Virtual Machine (KVM) for the Linux kernel, Xen, ESXi available from VMware, Windows Hyper-V available from Microsoft, and other open-source and proprietary hypervisors. Hypervisor 33 may represent a virtual machine manager (VMM). Hypervisor 333 includes a physical driver 335 to use the physical function provided by a network interface card.

Host device 228 may include authentication module 332. Module 332 may perform operations described using software, hardware, firmware, or a mixture of hardware, software, and firmware residing in and/or executing at host device 228. Host device 228 may execute module 332 with one or more processors. Host device 228 may execute module 332 as a virtual machine executing on underlying hardware. Module 332 may execute as a service or component of an operating system or computing platform. Module 332 may execute as one or more executable programs at an application layer of a computing platform. Module 332 may be otherwise arranged remotely to and remotely accessible to host device 228, for instance, as one or more network services operating at a network in a network cloud. In other words, module 332 may not be executing at host device 228. Instead, module 332 may be executing at a remote computing system (e.g., a server).

Authentication module 332 may be stored in long-term storage, such as storage 30. However, when authentication module 332 are executed by processor 14, processor 14 may read authentication module 332 into volatile memory, such as disk 31. Authentication module 332 may be stored in disk 31 throughout processor 14's execution of authentication module 332.

In accordance with the techniques of this disclosure, authentication module 332 may receive, either wired or wirelessly via a hub device in a secure domain, an authentication factor a biometric authentication device (e.g., biometric authentication device 220). Each respective authentication device in the plurality of authentication devices is in a non-secure domain. Further, each respective authentication factor comprises a respective identifier of a respective user of the respective authentication device. For instance, authentication module 332 may receive a retinal scan from an eye sensor worn or carried by the prospective user.

Authentication module 332 may determine whether the prospective user is a trusted user of the computing device based on the authentication factor. In doing so, authentication module 332 may compare the authentication factor to a previously registered authentication factor for the trusted user, the previously registered authentication factor being the stored authentication factors input by the user when establishing the user's profile in authentication factor data store 334. Authentication module 332 may then determine whether the authentication factor is within a threshold percentage of the previously registered authentication factor. If the respective authentication factor is within the threshold percentage of the previously registered authentication factor, authentication module 332 may classify the authentication factor as "valid" and determine that the prospective user is the trusted user. Conversely, if the respective authentication factor is not within the threshold percentage of the previously registered authentication factor, authentication module 332 may classify the authentication factor as "invalid" and deny access to host device 228 for the user.

In instances where the authentication factor is something inherent to the user's biology, the threshold percentage may be less than 100%, due to some variability in the ways user's biometrics are measured. For example, authentication module 332 may receive a vocal pattern from the user and determine that the vocal pattern may be an 80% match to a stored vocal pattern for the particular trusted user in authentication factor data store 334 due to some variations in the patterns. However, given that throat ailments, environmental noise, or oral obstructions may affect a user's voice, this may satisfy the threshold percentage for the vocal pattern authentication factor. Similarly, for fingerprints, dust or dirt on a housing of the authentication device or the user's finger may interfere with an accurate fingerprint reading. The threshold percentage may be even more lenient for authentication factors such as a motion gesture, where small variances in the size, speed, and orientation of the motion gesture may drastically affect the comparison to the stored motion gesture. In general, the threshold percentage for a baseline authentication factor may be any percentage where, given the natural chance for error when measuring the authentication factor, computing device 228 may be reasonably certain that the user is the particular trusted user.

In some examples, authentication module 332 may receive, either from user input or from a remote computing device, an indication of a number of authentication factors required to enable access to computing device 228. In such examples, authentication module 332 may enable access to computing device 332 if the number of valid authentication factors received is greater than or equal to the number of authentication factors required to enable access to computing device 228. For instance, in the example described above, if the number is one, authentication module 332 may enable access to computing device 228 if authentication module 332 classifies the vocal pattern of the user as "valid." In other examples, if the number is two, authentication module 332 may enable access to computing device 228 if authentication module 332 classifies both the fingerprint and the password as "valid." In some other examples, in order for authentication module 332 to grant access to computing device 228, each received authentication factor must be classified as "valid."

Responsive to determining that the prospective user of the biometric authentication device is the trusted user, authentication module 332 may enable access to one or more applications on computing device 228. Conversely, responsive to determining that the prospective user of the biometric authentication device is not the trusted user, authentication module 332 may disable access to the one or more applications on computing device 228. Authentication module 332 may either completely lock the device, or may otherwise limit access to computing device 228 such that the user may not utilize the full functionality of computing device 228. In some examples, specific reactivation procedures may be required at a central server to re-enable access to computing device 228. In other examples, authentication module 332 may re-enable access upon receiving authentication factors that authentication module 332 classifies as valid.

Authentication module 332 may intermittently request updates from the biometric authentication devices in order to continually verify the identity of the user accessing host device 228. In such instances, after confirming the identity of the user, authentication module 332 may send, to the biometric authentication device, a request for an updated authentication factor. After receiving the updated authentication factor, authentication module 332 may repeat the above authentication process. In other examples, the hub device may deny any outgoing communications to the biometric authentication devices. In such instances, the biometric authentication device may periodically indicate it is still valid by periodically sending the updated authentication factor without receiving the request. Authentication module 332 may repeat the above authentication process after receiving the updated authentication factor.

These techniques may use biometric identification parameters that, in combination, speed access to the client device while ensuring reliable, strong authentication. Biometric sensors that may be utilized with these techniques include a voice recognition sensor, an eye sensor, a facial recognition sensor, a motion sensor, a hand geometry sensor, a hand grip sensor, a fingerprint sensor, an electrocardiogram (ECG) sensor, an ear print sensor, or a gait sensor. The biometric authentication device may produce one or more of a voice pattern, a retinal scan, a facial recognition scan, a motion gesture, a hand geometry reading, a hand grip reading, a fingerprint, an electrocardiogram (ECG), an ear print, or a gait measurement.

In some examples, the authentication factors may also include information that identifies a user as being part of a particular group, and the access granted to the user is in line with general permissions granted to users of that group (e.g., the user is a medic, granting them access to medical information). In other examples, authentication factor data store 334 may, in addition to including the previously registered authentication factors, store permission information along with the user's identity information. For instance, authentication module 332 may determine that the trusted user has a medic credential based on information stored in authentication factor data store 334.

If authentication module 332 determines that the trusted user has the medic credential, authentication module 332 may enable the trusted user to access medical information for other users in the vicinity of the user. For instance, an allied user may require medical attention, and the allied user may be wearing an authentication device (similar to the biometric authentication device worn by the trusted user or a different authentication device, such as a finger tap sensor or radio frequency identification tag). The authentication device may read data from various respective sensors (e.g., a voice pattern, a finger tap sequence, a retinal scan, a motion gesture, a hand geometry reading, a hand grip reading, a fingerprint, an electrocardiogram (ECG), an ear print, a radio frequency identification tag, a gait measurement, and/or other authentication signals) to generate an authentication factor for the allied user. The biometric authentication device of the allied user may transmit the authentication factor to the hub device, which forwards the authentication factor to authentication module 332 upon ensuring the integrity of the authentication factors. Authentication module 332 may analyze the authentication factor to determine an identity of the allied user and retrieve medical information for the allied user by comparing the authentication factor to information stored in authentication factor data store 334. Authentication module 332 may display the medical information for review by the trusted user, enabling the trusted user to provide precise and effective medical care to the allied user in a physical location where access to a full medical history may be difficult.

For instance, the authentication factor for the allied user may be an ECG. Authentication module 332 may compare the ECG to one or more stored ECGs stored in authentication factor data store 334. Authentication module 332 may determine that a first stored ECG of the one or more stored ECGs most closely matches the ECG received from the biometric authentication device for the allied user. To provide additional security (e.g., for instances where the other user is not actually an allied user and an ECG for the other user is not in authentication factor data store 334), authentication module 332 may determine whether the ECG is within a threshold percentage of the first stored ECG. Responsive to determining that the received ECG is within a threshold percentage of the first stored ECG, authentication module 332 may determine that an identity associated with the first stored ECG is the identity of the allied user. Using this identity, authentication module 332 may retrieve the medical treatment information from authentication factor data store 334.

In other instances, the authentication factor received from the biometric authentication device of the allied user may be a data package that includes an indication of identity authentication (e.g., an indication of the allied user's identity from an RFID tag) and the medical treatment information. In such instances, authentication module 332 may determine the identity of the allied user based on a comparison between the indication of identity authentication and an identity of the allied user stored in authentication factor data store 334. If the indication of identity authentication matches the identity of the second prospective user stored in authentication factor data store 334, authentication module 332 may confirm the identity of the allied user. Based on this confirmation, authentication module 332 may determine that the medical treatment information included in the data package is valid and output the medical treatment information for display.

Figure 10:
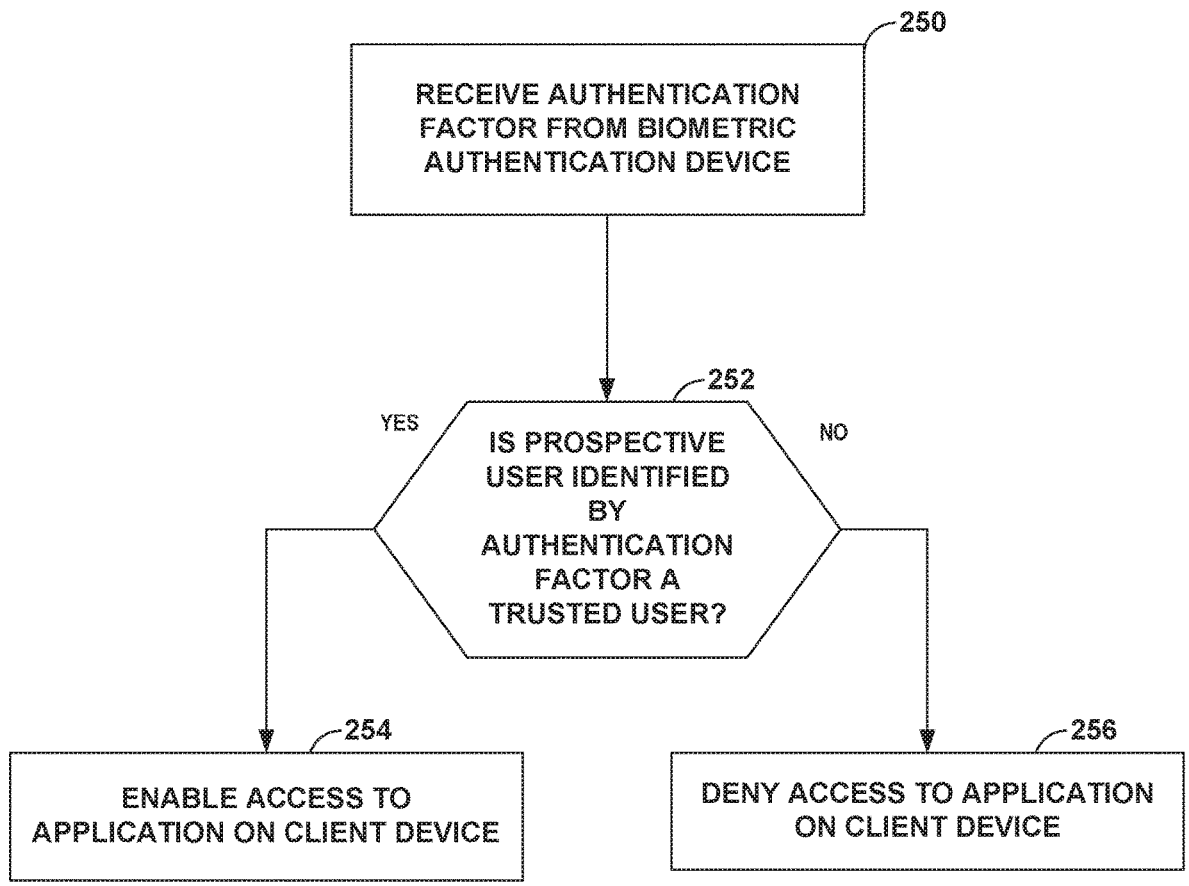
FIG. 10 is a flow diagram illustrating example operations of a server device that implements authentication techniques in accordance with one or more aspects of this disclosure.

FIG. 10 is a flow diagram illustrating example operations of a server device that implements authentication techniques in accordance with one or more aspects of this disclosure. The techniques of FIG. 10 may be performed by one or more processors of a computing device, such as host device 228 illustrated in FIG. 8 or host device 228 illustrated in FIG. 9. For purposes of illustration only, the techniques of FIG. 10 are described within the context of host device 228 of FIG. 9, although computing devices having configurations different than that of host device 228 may perform the techniques of FIG. 10. While the techniques described below with respect to FIG. 10 are described as being performed by processors 314 of host device 228, processors 314 may utilize other modules or applications, such as a virtual machine, to perform all or a portion of the techniques described herein, so as to maintain integrity between the secured data packets and the non-secured data packets.

In accordance with the techniques of this disclosure, processors 314 may receive, via a guard device in a secure domain, an authentication factor from a biometric authentication device in a non-secure domain (e.g., authentication devices 220) (250). The biometric authentication device is in a non-secure domain. Further, the authentication factor comprises a respective identifier of a prospective user of the biometric authentication device. Processors 314 may determine whether the prospective user is a trusted user of the computing device based on the authentication factor (252). Responsive to determining that the prospective user of the biometric authentication device is the trusted user (YES branch of 252), processors 314 may enable access to one or more applications on the client device (e.g., host 4 of FIG. 1) (254). Conversely, responsive to determining that the prospective user of the biometric authentication device is not the trusted user (NO branch of 252), processors 314 may disable access to the one or more applications on the computing device (256).

Processors 314 may intermittently request updates from the biometric authentication devices in order to continually verify the identity of the user accessing host device 228. In such instances, after confirming the identity of the user, processors 314 may send, to the biometric authentication device, a request for an updated authentication factor. After receiving the updated authentication factor, processors 314 may repeat the above authentication process.

These techniques may use biometric identification parameters that, in combination, speed access to the client device while ensuring reliable, strong authentication. Biometric sensors that may be utilized with these techniques include a voice recognition sensor, an eye sensor, a finger tap input sensor, a motion sensor, a hand geometry sensor, a hand grip sensor, a fingerprint sensor, an electrocardiogram (ECG) sensor, an ear print sensor, a radio frequency identification tag, or a gait sensor. The biometric authentication device may produce one or more of a voice pattern, a finger tap sequence, a retinal scan, a motion gesture, a hand geometry reading, a hand grip reading, a fingerprint, an electrocardiogram (ECG), an ear print, a radio frequency identification tag, or a gait measurement.

In some examples, the authentication factors may also include information that identifies a user as being part of a particular group, and the access granted to the user is in line with general permissions granted to users of that group (e.g., the user is a medic, granting them access to medical information). In other examples, the user database may, in addition to including the previously registered authentication factors, store permission information along with the user's identity information. For instance, processors 314 may determine that the trusted user has a medic credential based on information stored in the user database.

If processors 314 determines that the trusted user has the medic credential, processors 314 may enable the trusted user to access medical information for other users in the vicinity of the user. For instance, an allied user may require medical attention, and the allied user may be wearing a biometric authentication device (similar to the biometric authentication device worn by the trusted user). The biometric authentication device may read data from various respective sensors (e.g., a voice pattern, a finger tap sequence, a retinal scan, a motion gesture, a hand geometry reading, a hand grip reading, a fingerprint, an electrocardiogram (ECG), an ear print, a radio frequency identification tag, a gait measurement, and/or other authentication signals) to generate an authentication factor for the allied user. The biometric authentication device of the allied user may transmit the authentication factor to the hub device, which forwards the authentication factor to processors 314 upon ensuring the integrity of the authentication factors. Processors 314 may analyze the authentication factor to determine an identity of the allied user and retrieve medical information for the allied user by comparing the authentication factor to information stored in the user database. Processors 314 may display the medical information for review by the trusted user, enabling the trusted user to provide precise and effective medical care to the allied user in a physical location where access to a full medical history may be difficult.

By way of example, and not limitation, such computer-readable storage media can include RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the embodiment, certain acts or events of any of the methods described herein can be performed in a different sequence, may be added, merged, or left out altogether (e.g., not all described acts or events are necessary for the practice of the method). Moreover, in certain embodiments, acts or events may be performed concurrently, e.g., through multi-threaded processing, interrupt processing, or multiple processors, rather than sequentially.

In some examples, a computer-readable storage medium may include a non-transitory medium. The term "non-transitory" indicates that the storage medium is not embodied in a carrier wave or a propagated signal. In certain examples, a non-transitory storage medium may store data that can, over time, change (e.g., in RAM or cache).

Various examples of the disclosure have been described. Any combination of the described systems, operations, or functions is contemplated. These and other examples are within the scope of the following claims.

What is claimed is:

1. A method comprising:
   receiving, by a computing device in a secure domain, via a guard device, a first authentication factor from a biometric authentication device in a non-secure domain, wherein the first authentication factor comprises an identifier of a first prospective user of the biometric authentication device;

determining, by the computing device, whether the first prospective user is a trusted user of the computing device based on the first authentication factor;

determining, by the computing device, that the trusted user has a medic credential based on information stored in a user database stored on the computing device; and responsive to determining that the first prospective user of the biometric authentication device is the trusted user that has the medic credential, enabling, by the computing device, access to one or more applications on the computing device;

after enabling the access to the one or more applications on the computing device, receiving, by the computing device, via the guard device, a second authentication factor from a secondary authentication device in the non-secure domain, wherein the second authentication factor comprises an identifier of a second prospective user, wherein the second prospective user comprises a user of the secondary authentication device;

determining, by the computing device, an identity of the second prospective user based on the received second authentication factor and the information stored in the user database; and determining, by the computing device, medical treatment information about the second prospective user based on the identity of the second prospective user.

2. The method of claim 1, wherein receiving the first authentication factor comprises:

receiving, by the guard device via a first port, the first authentication factor from the biometric authentication device, wherein the biometric authentication device has a first security classification;

receiving, by the guard device via a second port, a data packet from a client device, wherein the second client device has a second security classification different than the first security classification; and sending, by the guard device via a third port, the first authentication factor and the data packet to the computing device.

3. The method of claim 1, wherein determining whether the first prospective user is the credentialed user of the computing device comprises:

comparing, by the computing device, the first authentication factor to a previously registered authentication factor for the trusted user; and responsive to determining that the first authentication factor is within a threshold percentage of the previously registered authentication factor, determining, by the computing device, that the first prospective user is the trusted user.

4. The method of claim 1, wherein the second authentication factor comprises an electrocardiogram, wherein determining the identity of the second prospective user comprises:

comparing, by the computing device, the electrocardiogram to one or more stored electrocardiograms stored in the user database;

determining, by the computing device, a first stored electrocardiogram that most closely matches the electrocardiogram of the second prospective user; and responsive to determining that the electrocardiogram is within a threshold percentage of the first stored electrocardiogram, determining, by the computing device, that an identity associated with the first stored electrocardiogram is the identity of the second prospective user.

5. The method of claim 4, wherein determining the medical treatment information about the second prospective user comprises:

retrieving, by the computing device, the medical treatment information from the user database.

6. The method of claim 1, wherein the second authentication factor comprises a data package comprising an indication of identity authentication and the medical treatment information, wherein determining the identity of the second prospective user comprises:

comparing, by the computing device, the indication of identity authentication with an identity of the second prospective user stored in the user database; and determining, by the computing device, the identity of the second prospective user if the indication of identity authentication matches the identity of the second prospective user stored in the user database.

7. The method of claim 6, wherein determining the medical treatment information about the second prospective user comprises:

retrieving, by the computing device, the medical treatment information from the data package.

8. The method of claim 1, wherein the biometric authentication device comprises one of a voice recognition sensor, a facial recognition sensor, an eye sensor, a motion sensor, a hand geometry sensor, a hand grip sensor, a fingerprint sensor, an electrocardiogram (ECG) sensor, an ear print sensor, or a gait sensor, and wherein the first authentication factor comprises one of a voice pattern, a facial recognition scan, a motion gesture, a retinal scan, a hand geometry reading, a hand grip reading, a fingerprint, an electrocardiogram (ECG), an ear print, or a gait measurement.

9. The method of claim 1, wherein the first authentication factor is received at a first time, wherein the method further comprises:

receiving, by the computing device, via the guard device at a second time later than the first time, a third authentication factor from the biometric authentication device;

determining, by the computing device, whether a user identified by the third authentication factor is the trusted user of the computing device identified by the first authentication factor based on the received third authentication factor;

responsive to determining that the user identified by the third authentication factor is the trusted user, continuing, by the computing device, to enable access to the one or more applications on the computing device; and responsive to determining that the user identified by the third authentication factor is not the trusted user, disabling, by the computing device, the access to the one or more applications on the computing device.

10. The method of claim 1, the method further comprising:

receiving, by the computing device, via the guard device, a third authentication factor from the biometric authentication device, wherein the first authentication factor is different than the third authentication factor;

determining, by the computing device, whether the first prospective user identified by the first authentication factor and a user identified by the third authentication factor are both the trusted user of the computing device based on the first authentication factor and the third authentication factor; and responsive to determining that the first prospective user identified by the first authentication factor and the user identified by the third authentication factor are both the trusted user of the computing device, enabling, by the computing device, access to one or more applications on the computing device.

11. A computing device comprising:
one or more communication units configured to receive, via a guard device, a first authentication factor from a biometric authentication device in a non-secure domain, wherein the first authentication factor comprises an identifier of a first prospective user of the biometric authentication device; and
one or more processors configured to:
determine whether the first prospective user is a trusted user of the computing device based on the first authentication factor;
determine that the trusted user has a medic credential based on information stored in a user database stored on the computing device; and
responsive to determining that the first prospective user of the biometric authentication device is the trusted user that has the medic credential, enable access to one or more applications on the computing device;
after enabling the access to the one or more applications on the computing device, receive via the guard device, a second authentication factor from a secondary authentication device in the non-secure domain, wherein the second authentication factor comprises an identifier of a second prospective user, wherein the second prospective user comprises a user of the secondary authentication device;
determine an identity of the second prospective user based on the received second authentication factor and the information stored in the user database; and
determine medical treatment information about the second prospective user based on the identity of the second prospective user.

12. The device of claim 11, wherein the one or more processors being configured to determine whether the first prospective user is a trusted user of the computing device based on the first authentication factor comprises the one or more processors being configured to:
compare the first authentication factor to a previously registered authentication factor for the trusted user; and
responsive to determining that the first authentication factor is within a threshold percentage of the previously registered authentication factor, determine that the first prospective user is the trusted user.

13. The device of claim 11, wherein the second authentication factor comprises an electrocardiogram, wherein the one or more processors being configured to determine the identity of the second prospective user comprises the one or more processors being configured to:
compare the electrocardiogram to one or more stored electrocardiograms stored in the user database;
determine a first stored electrocardiogram that most closely matches the electrocardiogram of the second prospective user; and
responsive to determining that the electrocardiogram is within a threshold percentage of the first stored electrocardiogram, determine that an identity associated with the first stored electrocardiogram is the identity of the second prospective user.

14. The device of claim 11, wherein the second authentication factor comprises a data package comprising an indication of identity authentication and the medical treatment information, wherein the one or more processors being configured to determine the identity of the second prospective user comprises the one or more processors being configured to:
compare the indication of identity authentication with an identity of the second prospective user stored in the user database; and
determine the identity of the second prospective user if the indication of identity authentication matches the identity of the second prospective user stored in the user database.

15. A non-transitory computer readable storage medium storing instructions that, when executed by one or more processors of a computing device, cause the one or more processors to:
receive, via a guard device, a first authentication factor from a biometric authentication device in a non-secure domain, wherein the computing device is in a secure domain, wherein the first authentication factor comprises an identifier of a first prospective user of the biometric authentication device;
determine whether the prospective user is a trusted user of the computing device based on the first authentication factor;
determine that the trusted user has a medic credential based on information stored in a user database stored on the computing device; and
responsive to determining that the prospective user of the biometric authentication device is the trusted user that has the medic credential, enable access to one or more applications on the computing device;
after enabling the access to the one or more applications on the computing device, receive via the guard device, a second authentication factor from a secondary authentication device in the non-secure domain, wherein the second authentication factor comprises an identifier of a second prospective user, wherein the second prospective user comprises a user of the secondary authentication device;
determine an identity of the second prospective user based on the received second authentication factor and the information stored in the user database; and
determine medical treatment information about the second prospective user based on the identity of the second prospective user.

* * * * *